US012630752B2

(12) United States Patent
Furukawa et al.

(10) Patent No.: US 12,630,752 B2
(45) Date of Patent: May 19, 2026

(54) EPOXY RESIN ADHESIVE FOR MEDICAL DEVICE AND CURED PRODUCT OF THE SAME, AND MEDICAL DEVICE MEMBER AND MEDICAL DEVICE

(71) Applicant: FUJIFILM Corporation, Tokyo (JP)

(72) Inventors: Kazushi Furukawa, Kanagawa (JP); Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 311 days.

(21) Appl. No.: 18/456,533

(22) Filed: Aug. 28, 2023

(65) Prior Publication Data

US 2023/0399554 A1 Dec. 14, 2023

Related U.S. Application Data

(63) Continuation of application No. PCT/JP2022/011960, filed on Mar. 16, 2022.

(30) Foreign Application Priority Data

Mar. 31, 2021 (JP) ................................ 2021-061463

(51) Int. Cl.
*C09J 163/00* (2006.01)
*A61B 1/00* (2006.01)
(Continued)

(52) U.S. Cl.
CPC ............... *C09J 163/00* (2013.01); *A61B 1/00* (2013.01); *A61B 1/0011* (2013.01); *C08K 3/38* (2013.01); *C08K 5/0025* (2013.01); *C08K 5/13* (2013.01); *C08K 5/17* (2013.01); *C09J 7/28* (2018.01); *C09J 11/06* (2013.01); *C09J 2301/408* (2020.08); *C09J 2400/163* (2013.01); *C09J 2463/00* (2013.01)

(58) Field of Classification Search
None
See application file for complete search history.

(56) References Cited

U.S. PATENT DOCUMENTS 9,822,287 B2 * 11/2017 Yokoyama ............ A61B 1/051
2021/0189203 A1 6/2021 Furukawa et al.
2021/0371715 A1 12/2021 Furukawa et al.

FOREIGN PATENT DOCUMENTS

EP 3150680 A1 * 4/2017 .......... C08G 59/504
JP H01304165 12/1989
(Continued)

OTHER PUBLICATIONS

"International Search Report (Form PCT/ISA/210) of PCT/JP2022/011960", mailed on May 24, 2022, with English translation thereof, pp. 1-5.
(Continued)

*Primary Examiner* — Frank D Ducheneaux
(74) *Attorney, Agent, or Firm* — JCIPRNET

(57) ABSTRACT

Provided are an epoxy resin adhesive for a medical device and its cured product, and a medical device member and a medical device. The epoxy resin adhesive includes the following components (A) to (C):

(A) an epoxy resin;
(B) a polyamine compound having two or more unsubstituted amino groups; and
(C) a compound having a nonaromatic carbon-carbon double bond group and a phenolic hydroxy group.

12 Claims, 1 Drawing Sheet

(51) Int. Cl.

| | |
|---|---|
| ***C08K 3/38*** | (2006.01) |
| ***C08K 5/00*** | (2006.01) |
| ***C08K 5/13*** | (2006.01) |
| ***C08K 5/17*** | (2006.01) |
| ***C09J 7/28*** | (2018.01) |
| ***C09J 11/06*** | (2006.01) |

(56) References Cited

FOREIGN PATENT DOCUMENTS

| | | |
|---|---|---|
| JP | H0363060 | 3/1991 |
| JP | 2007161811 | 6/2007 |
| JP | 2018095765 | 6/2018 |
| WO | 2020013003 | 1/2020 |
| WO | 2020175272 | 9/2020 |

OTHER PUBLICATIONS

"Written Opinion of the International Searching Authority (Form PCT/ISA/237) of PCT/JP2022/011960", mailed on May 24, 2022, with English translation thereof, pp. 1-6.

* cited by examiner

EPOXY RESIN ADHESIVE FOR MEDICAL DEVICE AND CURED PRODUCT OF THE SAME, AND MEDICAL DEVICE MEMBER AND MEDICAL DEVICE

CROSS-REFERENCE TO RELATED APPLICATIONS

This application is a Continuation of PCT International Application No. PCT/JP2022/011960 filed on Mar. 16, 2022, which claims priority under 35 U.S.C. § 119 (a) to Japanese Patent Application No. 2021-061463 filed in Japan on Mar. 31, 2021. Each of the above applications is hereby expressly incorporated by reference, in its entirety, into the present application.

BACKGROUND OF THE INVENTION

1. Field of the Invention

The present invention relates to an epoxy resin adhesive for a medical device and its cured product and to a medical device member and a medical device.

2. Description of the Related Art

Among adhesives, epoxy adhesives are particularly superior in workability and also in the adhesiveness, electrical properties, heat resistance, moisture resistance, etc. of their cured products. Epoxy adhesives are thus used in various fields, and research is ongoing on their potential use in securing constituent members of medical devices.

Medical devices used to examine or treat the human body require a high level of cleanliness and need to be cleaned and disinfected with chemicals after each use.

In particular, medical devices that are to be inserted into or applied to a blood vessel, the tracheas, the digestive tract, or other body cavity or tissue require a higher level of cleanliness achieved by sterilization, which is more rigorous than disinfection, so that bacterial infection will be prevented. A common sterilization process for such purposes is ethylene oxide gas (EOG) sterilization, and there is also a growing desire for the application of hydrogen peroxide plasma sterilization.

For example, WO2020/175272A describes an adhesive for an endoscope. The adhesive includes an epoxy resin including at least one of a bisphenol A epoxy resin, a bisphenol F epoxy resin, or a phenol novolac epoxy resin, a curing component, and an acid-based curing acceleration component. According to the technology described in WO2020/175272A, this adhesive for an endoscope gives, through a curing reaction, a cured product having superior gas barrier properties against sterilizing gases. Even repeated exposure to a sterilizing gas, furthermore, is unlikely to cause the cured product to degrade.

SUMMARY OF THE INVENTION

Certain medical devices are subjected to prolonged and repeated use. The secured state of a constituent member secured with the adhesive needs to be sufficiently maintained even after prolonged and repeated use of the medical device. In other words, there is a need not only for superior gas barrier properties, but also durability that allows the secured state to be sufficiently maintained even after repeated immersion in a disinfectant solution or repeated sterilization.

An object of the present invention is to provide an epoxy resin adhesive for a medical device. The epoxy resin adhesive is suitable for securing a constituent member of a medical device, has sufficiently high levels of characteristics that typical adhesives need to have (working life and shape retention before curing), and has rapid curability and viscosity suitable for the manufacture of a medical device. Another object of the present invention is to provide an adhesive and its cured product. The cured product, obtained through a curing reaction of the adhesive, is unlikely to degrade even when repeatedly immersed in a disinfectant solution and unlikely to exhibit a decrease in adhesiveness even when repeatedly sterilized. Yet another object of the present invention is to provide a medical device member having the cured product and a medical device including this medical device member. The medical device member is suitable for use as a constituent member of a medical device.

The objects of the present invention have been achieved by the following means.

<1>

An epoxy resin adhesive for a medical device, the epoxy resin adhesive including the following components (A) to (C):

(A) an epoxy resin;

(B) a polyamine compound having two or more unsubstituted amino groups; and (C) a compound having a nonaromatic carbon-carbon double bond group and a phenolic hydroxy group.

<2>

The epoxy resin adhesive for a medical device according to <1>, in which the nonaromatic carbon-carbon double bond group includes a vinyl group.

<3>

The epoxy resin adhesive for a medical device according to <1> or <2>, in which the component (C) includes a compound with an average degree of polymerization of 2 or greater.

<4>

The epoxy resin adhesive for a medical device according to any one of <1> to <3>, in which the component (C) includes a compound having a substituent in an ortho position with respect to a ring-forming carbon atom, in an aromatic hydrocarbon ring, to which the phenolic hydroxy group is bonded.

<5>

A cured product obtained by curing the epoxy resin adhesive for a medical device according to any one of <1> to <4>.

<6>

A medical device member having a metal substrate and the cured product according to <5> on the metal substrate.

<7>

The medical device member according to <6>, in which the metal substrate is a stainless steel substrate.

<8>

A medical device including a constituent member secured with the cured product according to <5>.

<9>

A medical device including, as a constituent member, the medical device member according to <6> or <7>.

<10>

The medical device according to <8> or <9>, in which the medical device is an endoscope.

In the present invention, the term phenolic hydroxy group refers to a hydroxy group bonded to a ring-forming carbon atom in an aromatic hydrocarbon ring.

In the present invention, multiple substituents, linking groups, or the like (hereinafter referred to as substituents or the like) represented by a particular symbol or formula, or multiple substituents or the like defined together, may be the same as or different from each other unless stated otherwise. This also applies to statements that specify the number of substituents or the like. Multiple substituents or the like close to (adjacent to in particular) each other may be linked together to form a ring unless stated otherwise. Unless stated otherwise, rings, such as aliphatic rings, aromatic rings, and heterocycles, may be fused together to form a fused ring.

In the present invention, a double bond that can have both the E and Z configurations in the molecule may be either E or Z unless stated otherwise. The double bond may even be a mixture of E and Z.

A representation of a compound herein includes any compound derived by partially changing the structure of the indicated compound unless the change interferes with the advantages of the present invention. A compound not explicitly described as being substituted or unsubstituted may have any substituent unless the substituent interferes with the advantages of the present invention. This also applies to substituents and linking groups. Of such optional substituents, substituents preferred in the present invention are substituents selected from substituent group T, described later.

In the present invention, range expressions like "(from) A to B," "between A and B," etc. are intended to include the values A and B as the lower and upper limits, respectively.

The epoxy resin adhesive for a medical device according to the present invention has sufficiently high levels of characteristics that typical adhesives need to have (working life and shape retention before curing) and rapid curability and viscosity suitable for the manufacture of a medical device. A cured product obtained through a curing reaction of the epoxy resin adhesive, furthermore, is unlikely to degrade even when repeatedly immersed in a disinfectant solution and unlikely to exhibit a decrease in adhesiveness even when repeatedly sterilized. The cured product according to the present invention and the medical device member according to the present invention, which has this cured product, are suitable for use as constituent members of a medical device because they are unlikely to degrade even when repeatedly immersed in a disinfectant solution and unlikely to exhibit a decrease in adhesiveness even when repeatedly sterilized. Including this medical device member, therefore, the medical device according to the present invention is superior in chemical resistance and sterilization durability and unlikely to exhibit a decrease in performance.

DESCRIPTION OF THE PREFERRED EMBODIMENTS

Figure 1:
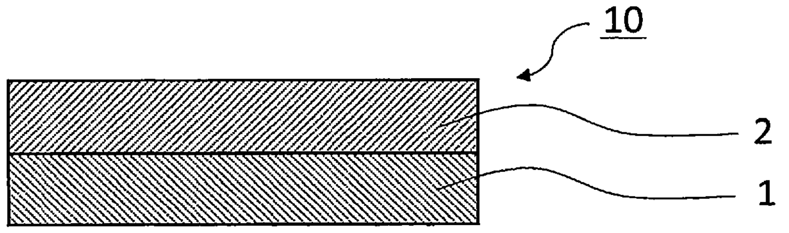
FIG. 1 is a cross-sectional view schematically illustrating an embodiment of a medical device member according to the present invention.

Epoxy Resin Adhesive for a Medical Device

A preferred embodiment of an epoxy resin adhesive for a medical device according to the present invention will now be described.

The epoxy resin adhesive for a medical device according to the present invention (hereinafter also referred to as "the adhesive according to the present invention) includes (A) an epoxy resin, (B) a polyamine compound having two or more unsubstituted amino groups, and (C) a compound having a nonaromatic carbon-carbon double bond group and a phenolic hydroxy group.

The epoxy resin (A) (hereinafter also simply referred to as "component (A)") is a base material for the adhesive. The polyamine compound (B) (hereinafter also simply referred to as "component (B)") is a curing component that reacts with the epoxy resin to cure the adhesive. The compound (C) having a nonaromatic carbon-carbon double bond group and a phenolic hydroxy group (hereinafter also simply referred to as "component (C)") is a component that can activate the epoxy groups in the epoxy resin to accelerate the curing reaction of the epoxy resin induced by the component (B) and also to cause the epoxy resin itself to form its homopolymer. For the adhesive according to the present invention, the amount of the compound (C) having a nonaromatic carbon-carbon double bond group and a phenolic hydroxy group as a ratio by mass is typically smaller than that of the curing component (B).

The form of the adhesive according to the present invention is not limited as long as it includes the above components. For example, the adhesive according to the present invention may contain a mixture of the components (A) to (C) (one-component form) or may include the components (A) to (C) with one or more of the components (A) to (C) separated from the rest (two-component form). Alternatively, the adhesive according to the present invention may include the components (A) to (C) with each of the components (A) to (C) separated from the others (three-component form). The adhesive according to the present invention encompasses all of these forms.

When the amounts of the components in the adhesive are described herein, or when the amounts of the components in the adhesive are specified in the present invention, such a description or specification means that, for the two-component or three-component form, the components (A) to (C) are mixed together for use in such a manner that the amount of each component in the mixture will be the desired amount as described above. This means that when the adhesive is in the two-component or three-component form and when its components are separate, the amounts of the components (A) to (C) do not need to be as described herein or as specified in the present invention. In other words, for the two-component or three-component form, such a description or specification means that the amounts of the components (A) to (C) are as described herein or as specified in the present invention after the mixing of the components (A) to (C) for use.

If the adhesive for a medical device according to the present invention is a one-component adhesive or if it is a two-component or similar adhesive yet with mutually reactive components mixed together (e.g., if the epoxy resin and the curing component have been mixed together), it is preferred to store the adhesive at a temperature low enough that the adhesive undergoes practically no reaction, so that the components will be kept stably maintained without reacting with each other or with their reactions inhibited to a sufficient extent. For example, the adhesive can be stored at −20° C. or lower. Preferably, the adhesive is stored at −30° C. or lower, more preferably −40° C. or lower, even more preferably −50° C. or lower. If necessary, the adhesive can be stored while being protected from light.

The adhesive according to the present invention can include, for example, solvents, plasticizers, adhesiveness enhancers (e.g., silane coupling agents), surfactants, colorants (e.g., pigments and dyes), antiweathering agents, antioxidants, heat stabilizers, lubricants, antistatic agents, whiteners, release agents, conductors, viscosity modifiers, fillers (e.g., silica and calcium carbonate), thixotropic agents, diluents, and flame retardants unless they interfere with the advantages of the present invention.

The epoxy resin adhesive for a medical device according to the present invention has sufficiently high levels of characteristics that typical adhesives need to have (working life and shape retention before curing) and rapid curability and viscosity suitable for the manufacture of a medical device. A cured product obtained through a curing reaction of the epoxy resin adhesive, furthermore, is unlikely to degrade even when repeatedly immersed in a disinfectant solution and unlikely to exhibit a decrease in adhesiveness even when repeatedly sterilized.

It is unclear why the epoxy resin adhesive for a medical device according to the present invention has rapid curability and viscosity suitable for the production of a medical device and why a cured product obtained through a curing reaction of the epoxy resin adhesive is unlikely to degrade even when repeatedly immersed in a disinfectant solution and unlikely to exhibit a decrease in adhesiveness even when repeatedly sterilized. A possible reason, however, is as follows.

The epoxy resin adhesive for a medical device according to the present invention contains an amine-based curing agent (component (B)), which is superior in rapid curability, in combination with a compound having a phenolic hydroxy group (component (C)), which has the ability to accelerate curing. This allows a high level of rapid curability suitable for the production of a medical device to be achieved. Hydrogen-bonding interactions between the amino groups in the amine-based curing agent and the phenolic hydroxy group, furthermore, restrict the movement of molecules. Presumably because of this, viscosity suitable for the production of a medical device can also be achieved.

The epoxy resin adhesive for a medical device according to the present invention also has a strong network resulting from hydrogen-bonding interactions between the amino groups in the amine-based curing agent and the phenolic hydroxy group. The cured product, therefore, is not easily permeable to components in the disinfectant. Presumably because of this, a cured product obtained through a curing reaction of the epoxy resin adhesive is unlikely to degrade even when repeatedly immersed in a disinfectant solution (superior in chemical resistance).

When a cured product of the epoxy resin adhesive according to the present invention is sterilized, for example, by hydrogen peroxide plasma sterilization, the cured product produces alkyl radicals. The alkyl radicals react with oxygen, producing peroxy radicals. The alkyl radicals are highly reactive with oxygen and become peroxy radicals immediately after being produced. In a cured product of the epoxy resin adhesive for a medical device according to the present invention, the compound having a nonaromatic carbon-carbon double bond group and a phenolic hydroxy group is presumably present near the network of the epoxy resin because of interactions between the phenolic hydroxy group and amino groups. By virtue of this, the nonaromatic carbon-carbon double bond group can effectively react with the alkyl radicals and capture them. Even if peroxy radicals are produced, it appears that they can be captured by the phenolic hydroxy group. This can be a reason why it is possible to inhibit degradation of the cured product and maintain its adhesiveness even when it is repeatedly sterilized (superior in sterilization durability).

The adhesive according to the present invention is used primarily to secure various members forming medical devices (medical device constituent members). More specifically, the adhesive according to the present invention is used to bond a medical device constituent member to another constituent member of the medical device and thereby to secure the medical device constituent member to the other constituent member of the medical device. The adhesive used to secure the medical device constituent member becomes a cured product that forms a bonded section of the medical device.

The member secured with the adhesive according to the present invention is not particularly limited. Examples of preferred members include metal members, glass members, and resin members. The "securing" of a medical device constituent member is carried out by bonding the medical device constituent member to another member forming the medical device (support member). The support member may be a tube wall or other portion of the medical device or an immovable member fastened to the pipe wall or other portion. Alternatively, the support member may be a member whose relative position inside the medical device can change, such as a tube. In the present invention, the term "secure" includes filling a space between a medical device constituent member and the support member to which this constituent member is to be joined with a cured product of the adhesive. That is, the term "secure" includes sealing.

A cured product of the adhesive according to the present invention itself can also be used as a medical device constituent member.

The individual components of the adhesive according to the present invention will now be described.

(A) Epoxy Resin

The adhesive according to the present invention includes an epoxy resin as the component (A). This epoxy resin preferably includes at least one of a bisphenol A epoxy resin, a bisphenol F epoxy resin, or a phenol novolac epoxy resin. The adhesive according to the present invention may include one epoxy resin selected from the group consisting of bisphenol A epoxy resins, bisphenol F epoxy resins, and phenol novolac epoxy resins alone or may include two or more.

The total percentage of bisphenol A epoxy resins, bisphenol F epoxy resins, and phenol novolac epoxy resins to the total amount of epoxy resin included in the adhesive according to the present invention is preferably 70% by mass or more, more preferably 80% by mass or more, even more preferably 90% by mass or more. It is particularly preferred that the epoxy resin present in the adhesive according to the present invention be at least one of a bisphenol A epoxy resin, a bisphenol F epoxy resin, or a phenol novolac epoxy resin.

The epoxy equivalent of the epoxy resin included in the adhesive according to the present invention is preferably from 10 to 1000, more preferably from 50 to 500, even more preferably from 80 to 400, particularly preferably from 100 to 300. The epoxy resin included in the adhesive according to the present invention typically has two or more epoxy groups per molecule.

The epoxy equivalent is a value determined by dividing the molecular weight of the epoxy compound by the number of moles of epoxy groups in the epoxy compound.

The bisphenol A epoxy resins that can be used in the adhesive according to the present invention are not particularly limited. A wide variety of bisphenol A epoxy resins commonly used as base materials for epoxy adhesives can be used. Preferred specific examples include bisphenol A diglycidyl ethers (jER 825, jER 828, and jER 834 (trade names), manufactured by Mitsubishi Chemical) and bisphenol A propoxylate diglycidyl ethers (manufactured by Signa-Aldrich).

The bisphenol F epoxy resins that can be used in the adhesive according to the present invention are not particularly limited. A wide variety of bisphenol F epoxy resins commonly used as base materials for epoxy adhesives can be used. Preferred specific examples include bisphenol F diglycidyl ethers (trade name, EPICLON 830; manufactured by DIC) and 4,4'-methylenebis(N,N-diglycidylaniline).

The phenol novolac epoxy resins that can be used in the adhesive according to the present invention are not particularly limited. A wide variety of phenol novolac epoxy resins commonly used as base materials for epoxy adhesives can be used. An example of such a phenol novolac epoxy resin is that commercially available from Sigma-Aldrich as Product No. 406775.

The amount of epoxy resin included in the adhesive according to the present invention can be from 5% to 90% by mass, more preferably from 10% to 75% by mass.

(B) Polyamine Compound having Two or More Unsubstituted Amino Groups

The adhesive according to the present invention contains a polyamine compound having two or more unsubstituted amino groups as the component (B) (hereinafter, a "polyamine compound having two or more unsubstituted amino groups" is also simply referred to as a "polyamine compound"). The adhesive according to the present invention may contain one component (B) alone or may contain two or more in combination.

More preferably, the polyamine compound is a primary polyamine compound (polyamine compound in which all amino groups are unsubstituted amino groups).

The polyamine compound preferably has two to ten, more preferably two to eight, even more preferably two to six, still more preferably two to four, particularly preferably two or three amino groups having an active hydrogen per molecule. In particular, at least one selected from the group consisting of diamine compounds and triamine compounds is suitable for use.

The active hydrogen equivalent (equivalent of active hydrogens in the amino groups) of the polyamine compound is preferably from 25 to 2000, more preferably from 25 to 550, even more preferably from 25 to 200, still more preferably from 25 to 100, still even more preferably from 25 to 85, particularly preferably from 27 to 40.

The active hydrogen equivalent is a value determined by dividing the molecular weight of the polyamine compound by the number of moles of active hydrogens in the amino groups in the polyamine compound (the term represents the molecular weight of the polyamine compound per active hydrogen in the amino groups).

The molecular weight of the polyamine compound is preferably from 100 to 6000, more preferably from 100 to 3000, even more preferably from 100 to 1000, particularly preferably from 100 to 500, particularly preferably from 100 to 300. If the polyamine compound is a polymer (e.g., if the polyamine compound has a polyoxyalkylene group as described later), the molecular weight is the number-average molecular weight.

The polyamine compound is preferably in a form in which two or more amino groups are coupled together by a group selected from the group consisting of aliphatic hydrocarbon groups, alicyclic hydrocarbon groups, aromatic hydrocarbon groups, and heterocyclic groups or a combination thereof. These groups may have a heteroatom, such as an oxygen, nitrogen, or sulfur atom (preferably, an oxygen atom), between carbon atoms.

To be less reactive with radicals produced in hydrogen peroxide plasma sterilization, the polyamine compound preferably includes no oxygen atom between carbon atoms, more preferably includes no heteroatom (atom that is not a carbon atom) between carbon atoms. Examples of heteroatoms include an oxygen atom, a nitrogen atom, and a sulfur atom.

If the polyamine compound includes no heteroatom between carbon-carbon bonds, it is preferred that the group coupling two or more amino groups together be a linear aliphatic hydrocarbon group, a combination of aliphatic hydrocarbon and aromatic hydrocarbon groups, or a combination of linear aliphatic hydrocarbon and alicyclic hydrocarbon groups, more preferably a linear aliphatic hydrocarbon group or a combination of linear aliphatic hydrocarbon and aromatic hydrocarbon groups, particularly preferably a linear aliphatic hydrocarbon group for further improved curability of the adhesive and further improved chemical resistance and sterilization durability of the cured product of the adhesive.

The linear aliphatic hydrocarbon group may have a branch. If the "group coupling amino groups together" is a linear aliphatic hydrocarbon group, it is preferred that this linear aliphatic hydrocarbon group have a branched structure.

The "combination of linear aliphatic hydrocarbon and aromatic hydrocarbon groups" is preferably, for example, a "linear aliphatic hydrocarbon group-aromatic hydrocarbon group-linear aliphatic hydrocarbon group."

Examples of "combinations of linear aliphatic hydrocarbon and alicyclic hydrocarbon groups" include a "linear aliphatic hydrocarbon group-alicyclic hydrocarbon group" and an "alicyclic hydrocarbon group-linear aliphatic hydrocarbon group-alicyclic hydrocarbon group."

The number of carbon atoms in a linear aliphatic hydrocarbon group is preferably from 4 to 50, more preferably from 4 to 12, even more preferably from 6 to 12. A linear aliphatic hydrocarbon group is preferably an alkylene group, and specific examples of alkylene groups include methylene, ethylene, hexamethylene, 2,4,4-trimethylhexamethylene, and dodecamethylene.

The number of carbon atoms in an alicyclic hydrocarbon group is preferably from 4 to 50, more preferably from 4 to 12, even more preferably from 6 to 12. An alicyclic hydrocarbon group is preferably a cycloalkylene group, and specific examples of cycloalkylene groups include cyclobutylene, cyclopentylene, and cyclohexylene.

Examples of aromatic hydrocarbon rings in an aromatic hydrocarbon group is a benzene ring and a fused ring formed by two or more benzene rings. Specific examples of such fused rings include a naphthalene ring, an anthracene ring, a perylene ring, a fluorene ring, and an acenaphthene ring. Of these aromatic hydrocarbon rings, a benzene ring is particularly preferred.

The polyamine compound may have an oxyalkylene structure. In that case, it is more preferred that the polyamine compound have a polyoxyalkylene structure.

The alkylene group in the oxyalkylene structure may be a linear alkylene group or may be an alkylene group having a branch. The number of carbon atoms in the alkylene group in the oxyalkylene structure is preferably from one to ten, more preferably from two to six, even more preferably from two to four.

More preferably, the oxyalkylene structure is an oxyethylene or oxypropylene group.

If the polyamine compound as the component (B) has a polyoxyalkylene structure, the multiple oxyalkylene groups forming this polyoxyalkylene structure may be the same as or different from each other. The average number of repetitions of the oxyalkylene group in the polyoxyalkylene structure is preferably from 2 to 1000, more preferably from 3 to 500. It is also preferred that this average number of repetitions be from 2 to 100, from 2 to 50, from 2 to 35, or from 2 to 25. The polyamine compound as the component (B) may have multiple polyoxyalkylene structures.

Preferred specific examples of polyamine compounds that can be used in the present invention are presented below. A number attached to parentheses or brackets represents the average number of repetitions of the parenthesized or bracketed repeating unit.

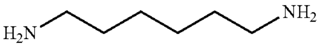
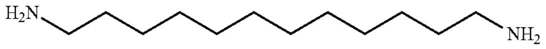
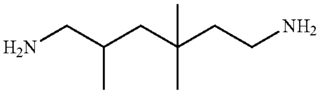
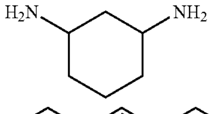
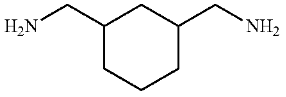
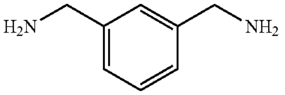
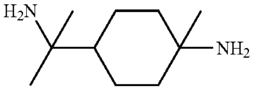
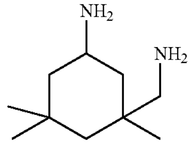
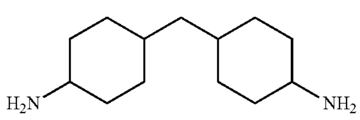
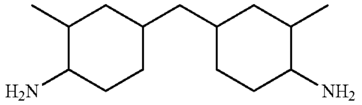
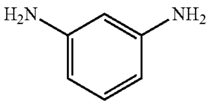
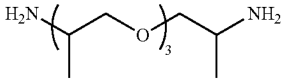
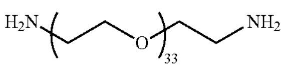
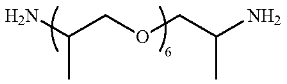
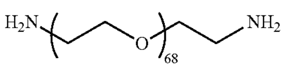
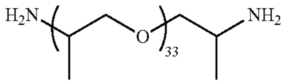
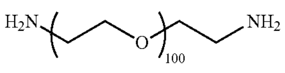
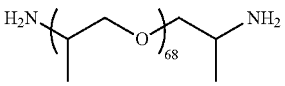
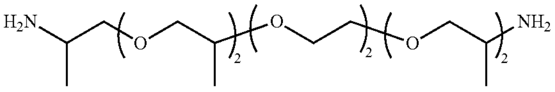
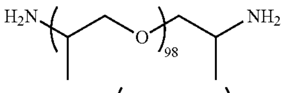
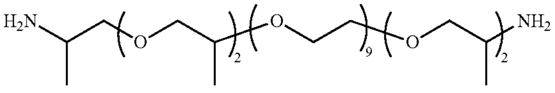

-continued

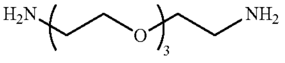
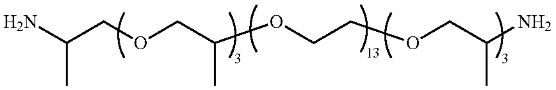
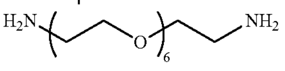
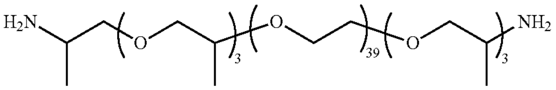
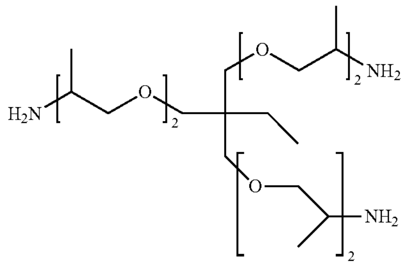
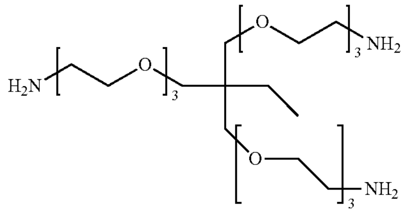
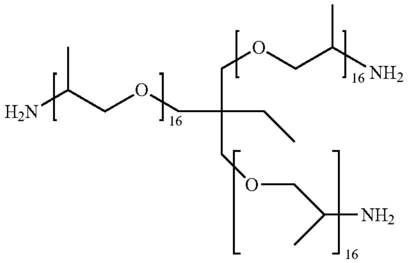
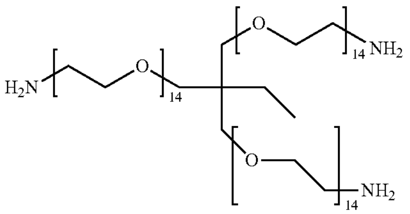
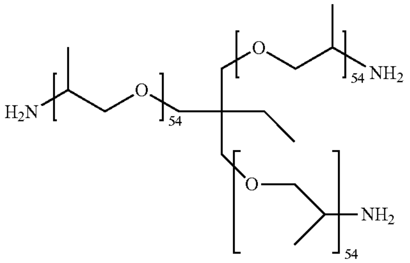
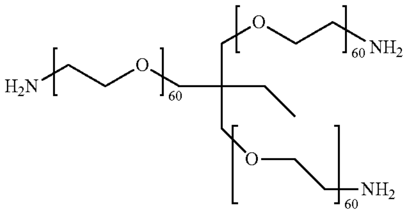

-continued
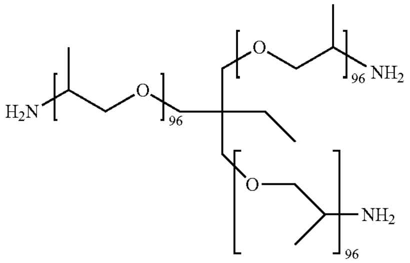
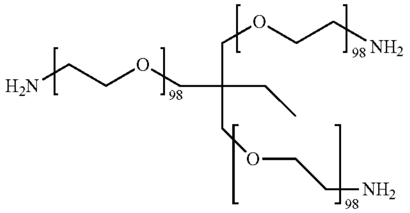
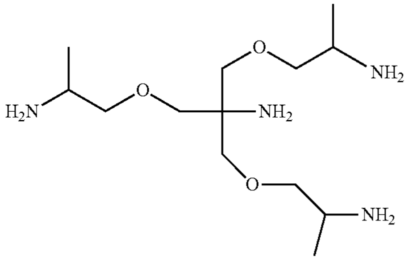
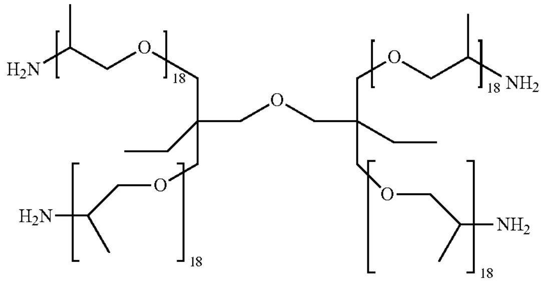
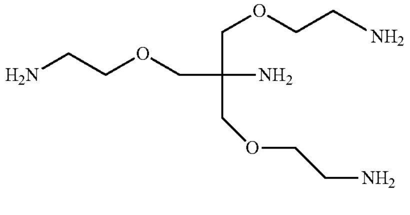
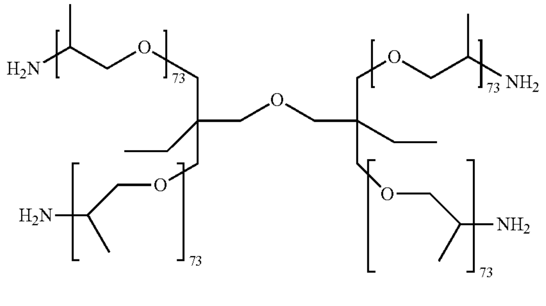
-continued
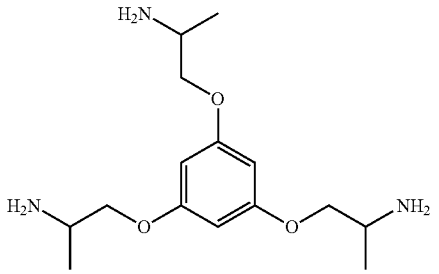
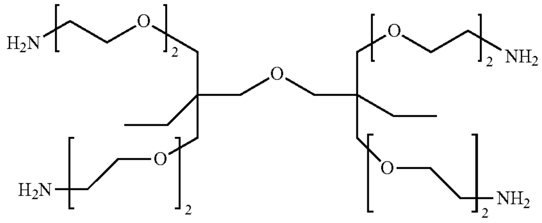
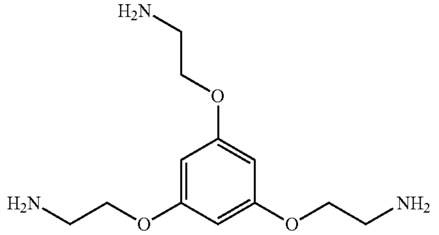
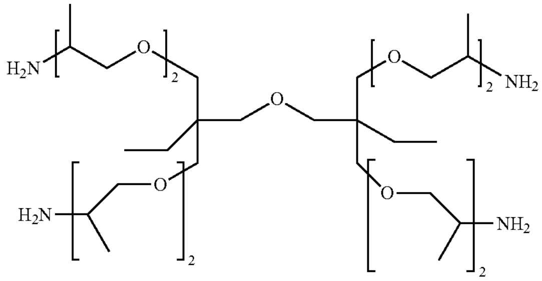
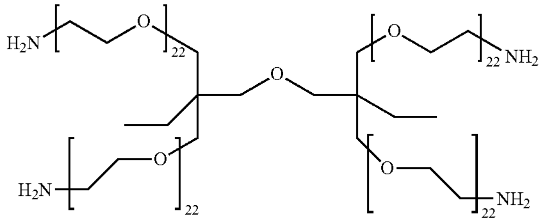
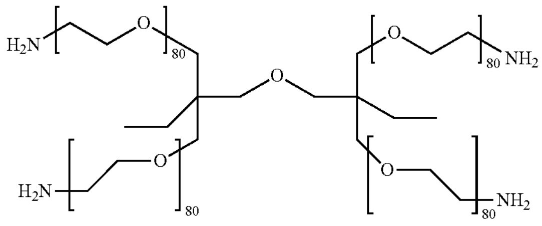
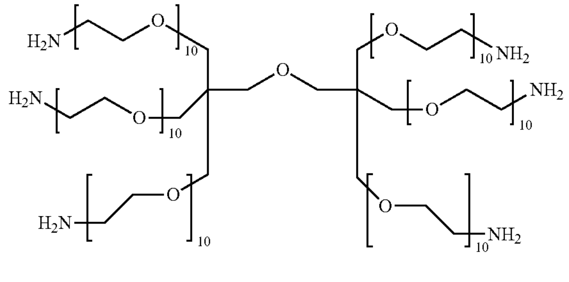

-continued

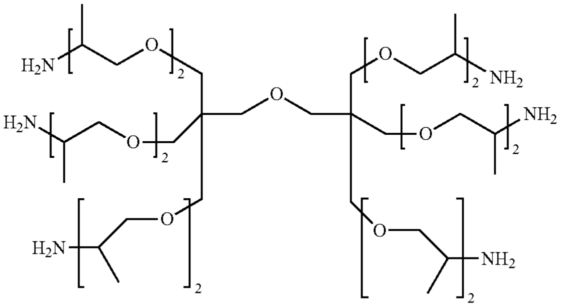

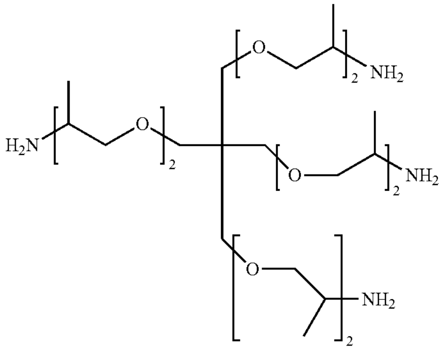

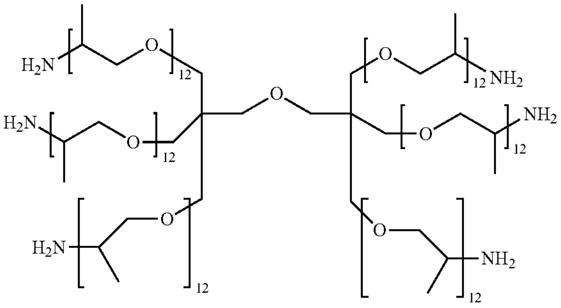

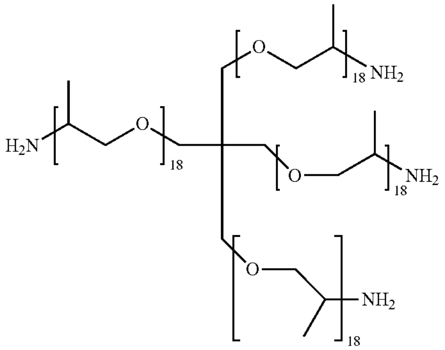

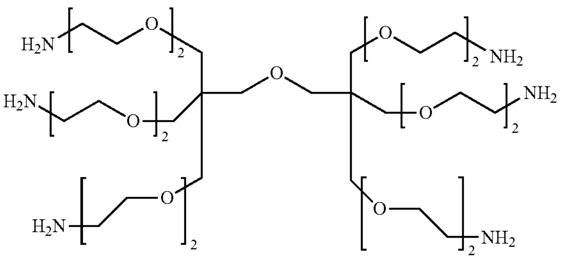

-continued

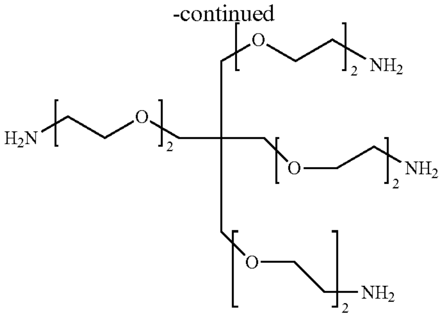

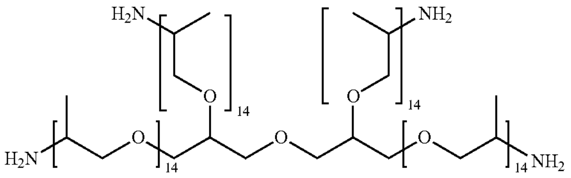

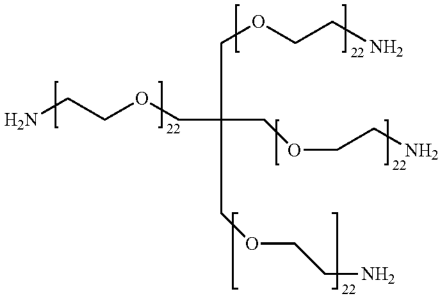

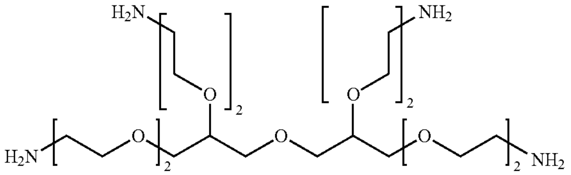

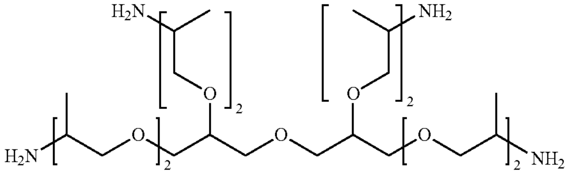

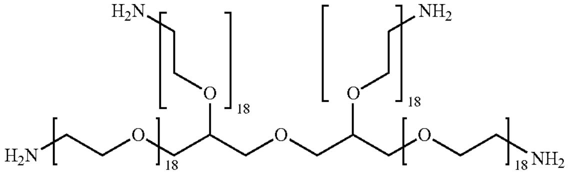

These polyamine compounds can be synthesized as usual. Commercially available polyamine compounds may also be used.

The amount of the component (B) in the adhesive according to the present invention is not particularly limited and can be adjusted as appropriate, for example, according to the reaction between the components (A) and (B).

The amount of the polyamine compound in the adhesive according to the present invention can be set as appropriate, for example, considering the active hydrogen equivalent.

For example, the amount of the polyamine compound can be from 5 to 100 parts by mass, more preferably is from 8 to 75 parts by mass, even more preferably from 10 to 50 parts by mass per 100 parts by mass of the epoxy resin as the component (A). It is, furthermore, preferred that the polyamine compound be used with the ratio of its active hydrogen equivalent to the epoxy equivalent of the epoxy resin as the component (A) (active hydrogen equivalent/epoxy equivalent) being from 0.1 to 1.5. More preferably, this ratio is from 0.3 to 1.0, even more preferably from 0.5 to 1.0.

(C) Compound having a Nonaromatic Carbon-Carbon Double Bond Group and a Phenolic Hydroxy Group The adhesive according to the present invention contains a compound having a nonaromatic carbon-carbon double bond group and a phenolic hydroxy group as the component (C). A "compound having a nonaromatic carbon-carbon double bond group and a phenolic hydroxy group" may be hereinafter simply referred to as a "phenolic compound."

The adhesive according to the present invention may contain one component (C) alone or two or more in combination.

The nonaromatic carbon-carbon double bond group is not particularly limited as long as it is a monovalent group including a nonaromatic carbon-carbon double bond. The number of carbon atoms in it is preferably from 3 to 20, more preferably from 3 to 10. The nonaromatic carbon-carbon double bond group is preferably a group having a terminal vinyl group.

Specific examples of nonaromatic carbon-carbon double bond groups include alkenyl groups (preferably having 3 to 20 carbon atoms, more preferably 3 to 10 carbon atoms, even more preferably 3 to 5 carbon atoms), alkenylcarbonyloxy groups (preferably having 3 to 20 carbon atoms, more preferably 3 to 10 carbon atoms, even more preferably 3 to 5 carbon atoms), and alkenyloxy groups (preferably having 3 to 20 carbon atoms, more preferably 3 to 10 carbon atoms).

The phenolic compound may have a substituent that is not a nonaromatic carbon-carbon double bond group. An example of this substituent is a substituent selected from substituent group T described below (but not a substituent including a nonaromatic carbon-carbon double bond group). The phenolic compound typically has no epoxy group.

For the phenolic compound, it is preferred that the nonaromatic carbon-carbon double bond group and at least one substituent that is not a nonaromatic carbon-carbon double bond group be linked to the ortho positions with respect to the ring-forming carbon atom, in the aromatic hydrocarbon ring, to which the phenolic hydroxy group is bonded. The presence of the phenolic hydroxy group in a bulky environment increases the ability of the component (C) to trap peroxy radicals, so that the sterilization durability of the cured product can be enhanced.

Examples of substituents that are not nonaromatic carbon-carbon double bond groups include alkyl groups (preferably having 3 to 20 carbon atoms, more preferably 3 to 10 carbon atoms), aryl groups (preferably having 6 to 30 carbon atoms, more preferably 6 to 20 carbon atoms), alkoxy groups (preferably having 3 to 20 carbon atoms, more preferably 3 to 10 carbon atoms), aryloxy groups (preferably having 6 to 30 carbon atoms, more preferably 6 to 20 carbon atoms), acyloxy groups (preferably having 3 to 20 carbon atoms, more preferably 3 to 10 carbon atoms), and alkoxycarbonyloxy groups (preferably having 3 to 20 carbon atoms, more preferably 3 to 10 carbon atoms).

The phenolic compound may have one type of nonaromatic carbon-carbon double bond group alone or two or more types in combination. The phenolic compound may have one phenolic hydroxy group or may have two or more. The phenolic compound may be a low-molecular-weight compound or may be a polymer, preferably is a polymer because in that case migration from the cured product is less likely, preferably a polymer having an average degree of polymerization of 2 or greater. The average degree of polymerization is preferably 1.05 or greater, more preferably 1.5 or greater. It is practical that the average degree of polymerization be 10 or less.

The molecular weight of the phenolic compound (low-molecular-weight compound) is not particularly limited and preferably is 100 or more and less than 2000, more preferably 120 or more and 1000 or less, even more preferably 120 or more and 500 or less. By setting the molecular weight within these ranges, it is possible to reduce the likelihood of migration of the phenolic compound from the cured product and achieve sufficient solubility in the epoxy resin as the component (A).

The weight-average molecular weight of the polymer is not particularly limited. For example, it can be from 200 to 2000, preferably is from 200 to 500.

The weight-average or number-average molecular weight of a compound described herein is determined as follows.

The weight-average or number-average molecular weight can be measured as a polystyrene-equivalent molecular weight by gel permeation chromatography (GPC).

Specifically, HLC-8220 GPC device (trade name, manufactured by Tosoh) is used. The eluant is tetrahydrofuran, and the column is TSKgel Super AWM-H (trade name, manufactured by Tosoh). At 23° C., detection is performed using UV with the flow rate ranging from 0.3 to 0.5 mL/min.

Examples of phenolic compounds include compounds represented by formula (1) or (2) below and polymers having a constituent component represented by formula (3) below. Polymers having a constituent component represented by formula (3) below as a repeating unit are preferred.

Formula (1)

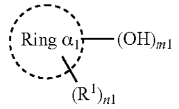

Formula (2)

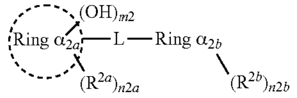

Formula (3)

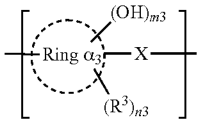

In these formulae, $R^1$, $R^{2a}$, $R^{2b}$, and $R^3$ represent substituents. L represents a divalent linking group. X represents a single bond or divalent linking group. Rings $\alpha_1$, $\alpha_{2a}$, $\alpha_{2b}$, and $\alpha_3$ represent aromatic hydrocarbon rings. m1 to m3 are integers of 1 or greater. n1, n2b, and n3 are integers of 1 or greater. n2a is 0 or an integer of 1 or greater. The upper limits of m1+n1, m2+n2a, n2b, and m3+n3 are the maximum numbers of substituents that rings $\alpha_1$, $\alpha_{2a}$, $\alpha_{2b}$, and $\alpha_3$, respectively, can have.

It should be noted that in formula (1), at least one $R^1$ represents a nonaromatic carbon-carbon double bond group. In formula (2), at least one of $R^{2a}$ or $R^{2b}$ represents a nonaromatic carbon-carbon double bond group. In formula (3), at least one $R^3$ represents a nonaromatic carbon-carbon double bond group. Preferably, in formula (1), one to three $R^1$s represent nonaromatic carbon-carbon double bond groups, in formula (2), one to three $R^{2b}$s represent nonaromatic carbon-carbon double bond groups, and in formula (3), one to three $R^3$s represent nonaromatic carbon-carbon double bond groups. More preferably, in formula (1), one $R^1$ represents a nonaromatic carbon-carbon double bond group, in formula (2), one $R^{2b}$ represents a nonaromatic carbon-carbon double bond group, and in formula (3), one $R^3$ represents a nonaromatic carbon-carbon double bond group.

An example of a substituent that can be chosen as $R^1$, $R^{2a}$, $R^{2b}$, and $R^3$ is a substituent selected from substituent group T described below. Examples of preferred substituents include an alkyl group, an aryl group, a heterocyclic group, an alkoxy group, an acyl group, an alkoxycarbonyl group, an aryloxycarbonyl group, an alkylsulfonyl group, an arylsulfonyl group, a cyano group, a nitro group, and —$Si(R^7)_3$. $R^7$ represents an alkyl, aryl, alkoxy, or aryloxy group. The three $R^7$s may be the same as or different from each other.

The alkyl, aryl, heterocyclic, alkoxy, acyl, alkyloxycarbonyl, aryloxycarbonyl, alkylsulfonyl, and arylsulfonyl groups that can be chosen as $R^1$, $R^{2b}$, $R^{2b}$, and $R^3$ have the same meaning as in the description of the respective groups in Substituent Group T below. Their preferred forms are also the same.

Each of these groups that can be chosen as $R^1$, $R^{2a}$, $R^{2b}$, and $R^3$ may be an unsubstituted group or may be a group having a substituent. The substituent that each of the groups that can be chosen as $R^1$, $R^{2a}$, $R^{2b}$, and $R^3$ may have is not particularly limited. If each of the groups that can be chosen as $R^1$, $R^{2a}$, $R^{2b}$, and $R^3$ has a substituent, the number of substituents that each group has can be, for example, four or less.

If n1, n2a, n2b, and n3 are integers of 2 or greater and if the multiple $R^1$s, $R^{2a}$s, $R^{2b}$s, and $R^3$s are adjacent to each other and at positions at which they can be bonded together, these substituents may be bonded together to form any of a five- to seven-membered ring or a spiro or bicyclo ring.

The alkyl, aryl, alkoxy, and aryloxy groups that can be chosen as $R^7$ have the same meaning as in the description of the respective groups in Substituent Group T below. Their preferred forms are also the same as described in Substituent Group T below.

Each of these groups that can be chosen as $R^7$ may be an unsubstituted group or may be a group having a substituent. The substituent that each of the groups that can be chosen as $R^7$ may have is not particularly limited. Preferably, the substituent is selected from substituent group T described below. If each of the groups that can be chosen as $R^7$ has a substituent, the number of substituents is not particularly limited as long as it is 1 or greater. For example, it can be four or less.

Examples of substituents that can be chosen as $R^1$, $R^{2a}$, $R^{2b}$, and $R^3$ excluding nonaromatic carbon-carbon double bond groups include alkyl groups (preferably having 3 to 20 carbon atoms, more preferably 3 to 10 carbon atoms), aryl groups (preferably having 6 to 30 carbon atoms, more preferably 6 to 20 carbon atoms), alkoxy groups (preferably having 3 to 20 carbon atoms, more preferably 3 to 10 carbon atoms), aryloxy groups (preferably having 6 to 30 carbon atoms, more preferably 6 to 20 carbon atoms), acyloxy groups (preferably having 3 to 20 carbon atoms, more preferably 3 to 10 carbon atoms), and alkoxycarbonyloxy groups (preferably having 3 to 20 carbon atoms, more preferably 3 to 10 carbon atoms). Alkyl groups are preferred.

Examples of preferred divalent linking groups that can be chosen as X include an alkylene group, an arylene group, and a heterocyclic group.

The alkylene, arylene, and heterocyclic groups that can be chosen as X have the same meaning as the groups that form when another hydrogen atom is removed from alkyl groups, aryl groups, and heterocyclic groups, respectively, selected from substituent group T described below. Their preferred forms are also the same.

Each of these groups that can be chosen as X may be an unsubstituted group or may be a group having a substituent. The substituent that each of the groups that can be chosen as X may have is not particularly limited. Preferably, the substituent is selected from substituent group T described below. If each of the groups that can be chosen as X has a substituent, the number of substituents is not particularly limited as long as it is one or greater. For example, it can be four or less.

In particular, if a linear linking chain, with which the number of carbon atoms forming the linkage (i.e., the number of atoms that link rings $\alpha_3$ of adjacent repeating units together) is the smallest, is assumed for each of the groups that can be chosen as X, the smallest number of carbon atoms in this linking chain is preferably from 1 to 50, more preferably from 1 to 20, even more preferably from 1 to 6.

X is preferably a single bond, alkylene group, arylene group, or heterocyclic group, more preferably a single bond or alkylene group, even more preferably an alkylene group.

Examples of aromatic hydrocarbon rings that can be chosen as rings $\alpha_1$, $\alpha_{2a}$, $\alpha_{2b}$, and $\alpha_3$ include a benzene ring and a fused ring formed by two or more benzene rings. Specific examples of such fused rings include a naphthalene ring, an anthracene ring, a perylene ring, a fluorene ring, and an acenaphthene ring. Of these aromatic hydrocarbon rings, a benzene ring is particularly preferred.

The upper limits of m1 to m3 and the upper limits of n1, n2a, n2b, and n3 are not particularly limited as long as the totals (m1+n1, m2+n2a, n2b, and m3+n3) are equal to or smaller than the maximum numbers of substituents that rings $\alpha_1$, $\alpha_{2a}$, $\alpha_{2b}$, and $\alpha_3$, respectively, can have. Each of m1 to m3 is preferably from 1 to 5, more preferably from 1 to 3, even more preferably 1 or 2. n1, n2a, n2b, and n3 are preferably from 1 to 5, more preferably from 1 to 3, even more preferably 1 or 2.

Substituent Group T

In the present invention, an example of a preferred substituent is a substituent selected from substituent group T described below.

If a substituent is described simply as a substituent herein, this substituent group T is referred to. If a particular group, such as an alkyl group, is simply mentioned, the corresponding group in this substituent group T is preferred for application.

If an alkyl group is mentioned separately from a cyclic (cyclo-)alkyl group herein, the alkyl group is intended to encompass linear and branched alkyl groups. If an alkyl group is not mentioned separately from a cyclic alkyl group, the alkyl group is intended to encompass a linear alkyl group, a branched alkyl group, and a cycloalkyl group unless stated otherwise. The same applies to groups (e.g., alkoxy, alkylthio, and alkenyloxy groups) that include a group that can have a ring structure (e.g., an alkyl, alkenyl, or alkynyl group) and to compounds that include a group that can have a ring structure. If a group can form a cyclic skeleton, the lower limit of the number of atoms in the group forming a cyclic skeleton is three or more, preferably five or more, independently of the lower limits of the numbers of atoms specified below in relation to groups that can have this structure.

In the following description of substituent group T, groups having a linear or branched structure and groups having a ring structure may be described separately, like alkyl groups and cycloalkyl groups, so that they can be clearly differentiated.

The groups included in substituent group T include the following groups.

The groups include alkyl groups (preferably having 1 to 30 carbon atoms, more preferably 1 to 20 carbon atoms, even more preferably 1 to 12 carbon atoms, still more preferably 1 to 8 carbon atoms, still even more preferably 1 to 6 carbon atoms, particularly preferably 1 to 3 carbon atoms), alkenyl groups (preferably having 2 to 30 carbon atoms, more preferably 2 to 20 carbon atoms, even more preferably 2 to 12 carbon atoms, still more preferably 2 to 6 carbon atoms, still even more preferably 2 to 4 carbon atoms), alkynyl groups (preferably having 2 to 30 carbon atoms, more preferably 2 to 20 carbon atoms, even more preferably 2 to 12 carbon atoms, still more preferably 2 to 6 carbon atoms, still even more preferably 2 to 4 carbon atoms), cycloalkyl groups (preferably having 3 to 20 carbon atoms), cycloalkenyl groups (preferably having 5 to 20 carbon atoms), aryl groups (an aryl group may be a monocyclic group or may be a fused-ring group (preferably a fused-ring group having two to six rings); a fused-ring group is composed of, for example, five- to seven-membered rings; an aryl group preferably has 6 to 40 carbon atoms, more preferably 6 to 30 carbon atoms, even more preferably 6 to 26 carbon atoms, particularly preferably 6 to 10 carbon atoms), heterocyclic groups (a heterocyclic group has at least one nitrogen, oxygen, sulfur, phosphorus, silicon, or selenium atom as a ring-forming atom and may be a monocyclic group or may be a fused-ring group (preferably a fused-ring group having two to six rings); the ring size of a monocyclic group is preferably five to seven, more preferably five or six; the number of carbon atoms in a heterocyclic group is preferably from 2 to 40, more preferably from 2 to 20; the heterocyclic groups encompass aromatic heterocyclic groups (heteroaryl groups) and aliphatic heterocyclic groups (aliphatic heteroatom-containing groups)), alkoxy groups (preferably having 1 to 20 carbon atoms, more preferably 1 to 12 carbon atoms), alkenyloxy groups (preferably having 2 to 20 carbon atoms, more preferably 2 to 12 carbon atoms), alkynyloxy groups (preferably having 2 to 20 carbon atoms, more preferably 2 to 12 carbon atoms), cycloalkyloxy groups (preferably having 3 to 20 carbon atoms), aryloxy groups (preferably having 6 to 40 carbon atoms, more preferably 6 to 26 carbon atoms, even more preferably 6 to 14 carbon atoms), heterocyclic oxy groups (preferably having 2 to 20 carbon atoms), alkoxycarbonyl groups (preferably having 2 to 20 carbon atoms), cycloalkoxycarbonyl groups (preferably having 4 to 20 carbon atoms), aryloxycarbonyl groups (preferably having 6 to 20 carbon atoms), amino groups (preferably having 0 to 20 carbon atoms and including an unsubstituted amino group (—$NH_2$), (mono- or di-)alkylamino groups, (mono- or di-)alkenylamino groups, (mono- or di-)alkynylamino groups, (mono- or di-)cycloalkylamino groups, (mono- or di-)cycloalkenylamino groups, (mono- or di-)arylamino groups, and (mono- or di-)heterocyclic amino groups; each of the groups substituting an unsubstituted amino group has the same meaning as the corresponding group in substituent group T), sulfamoyl groups (preferably having 0 to 20 carbon atoms; alkyl, cycloalkyl, or aryl sulfamoyl groups are preferred), acyl groups (preferably having 1 to 20 carbon atoms, more preferably 2 to 15 carbon atoms), acyloxy groups (preferably having 1 to 20 carbon atoms), carbamoyl groups (preferably having 1 to 20 carbon atoms; alkyl, cycloalkyl, or aryl carbamoyl groups are preferred), acylamino groups (preferably having 1 to 20 carbon atoms), sulfonamide groups (preferably having 0 to 20 carbon atoms; alkyl, cycloalkyl, or aryl sulfonamide groups are preferred), alkylthio groups (preferably having 1 to 20 carbon atoms, more preferably 1 to 12 carbon atoms), cycloalkylthio groups (preferably having 3 to 20 carbon atoms), arylthio groups (preferably having 6 to 40 carbon atoms, more preferably 6 to 26 carbon atoms, even more preferably 6 to 14 carbon atoms), heterocyclic thio groups (preferably having 2 to 20 carbon atoms), alkylsulfonyl, cycloalkylsulfonyl, or arylsulfonyl groups (preferably having 1 to 20 carbon atoms), silyl groups (preferably having 1 to 30 carbon atoms, more preferably 1 to 20 carbon atoms; alkyl-, aryl-, alkoxy-, or aryloxy-substituted silyl groups are preferred), silyloxy groups (preferably having 1 to 20 carbon atoms; alkyl-, aryl-, alkoxy-, or aryloxy-substituted silyloxy groups are preferred), a hydroxy group, a cyano group, a nitro group, halogen atoms (e.g., a fluorine, chlorine, bromine, or iodine atom), an oxygen atom (specifically, a >$CH_2$ forming the ring is replaced with >C═O), a carboxy group (—$CO_2H$), a phosphono group [—$PO(OH)_2$], a phosphoryl group [—O—$PO(OH)_2$], a sulfo group (—$SO_3H$), a borate group [—$B(OH)_2$], onio groups (including ammonio groups including cyclic ammonio, sulfonio groups, and phosphonio groups and preferably having 0 to 30 carbon atoms, more preferably 1 to 20), a sulfanyl group (—SH), amino acid residues, and polyamino acid residues.

Also included are the above alkyl, alkenyl, alkynyl, cycloalkyl, cycloalkenyl, aryl, heterocyclic, alkoxy, alkenyloxy, alkynyloxy, cycloalkyloxy, aryloxy, heterocyclic oxy, alkoxycarbonyl, cycloalkoxycarbonyl, aryloxycarbonyl, amino, sulfamoyl, acyl, acyloxy, carbamoyl, acylamino, sulfonamide, alkylthio, cycloalkylthio, arylthio, heterocyclic thio, and alkylsulfonyl, cycloalkylsulfonyl, or arylsulfonyl groups having a carboxy group, phosphono group, sulfo group, onio group, amino acid residue, or polyamino acid residue as a substituent.

The substituent selected from substituent group T is more preferably an alkyl group, alkenyl group, cycloalkyl group, aryl group, heterocyclic group, alkoxy group, cycloalkoxy group, aryloxy group, alkoxycarbonyl group, cycloalkoxycarbonyl group, amino group, acylamino group, cyano group, or halogen atom, particularly preferably an alkyl group, alkenyl group, aryl group, heterocyclic group, alkoxy group, alkoxycarbonyl group, amino group, acylamino group, or cyano group.

Unless stated otherwise, substituents selected from substituent group T include groups that are combinations of multiple ones of the above groups. For instance, when a compound or substituent, for example, includes an alkyl, alkenyl, or similar group, such groups may be substituted or unsubstituted. When aryl, heterocyclic, and similar groups are included, these groups may be monocyclic or fused rings and may be substituted or unsubstituted.

In a polymer having a constituent component represented by formula (3) above, the amount of the constituent component represented by formula (3) above is not particularly limited, but for example, it is preferably 70% by mass or more, more preferably 80% by mass or more, even more preferably 90% by mass or more of all constituent components forming the polymer.

The other constituent components forming the polymer, other than formula (3) above, are not particularly limited.

The phenolic hydroxy group equivalent of the phenolic compound is preferably from 100 to 400, more preferably from 100 to 300. By setting the phenolic hydroxy group equivalent within these ranges, it is possible to prevent polarity from being too high, achieve sufficient solubility in the epoxy resin as the component (A), and achieve a sufficiently strong curing acceleration effect.

The phenolic hydroxy group equivalent is a value determined by dividing the molecular weight of the phenolic compound by the number of moles of phenolic hydroxy groups in the epoxy compound.

Preferred specific examples of phenolic compounds that can be used in the present invention are presented below. The number attached to the brackets represents the average number of repetitions of the bracketed repeating unit.

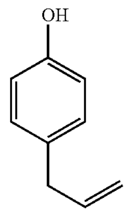

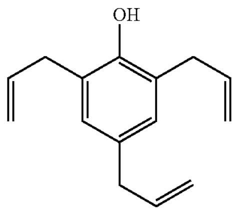

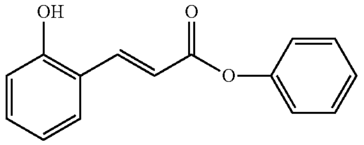

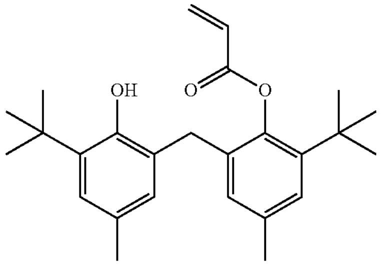

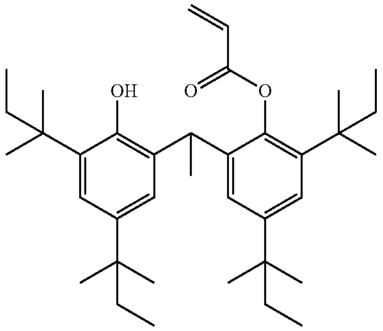

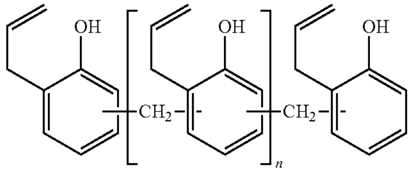

These phenolic compounds can be synthesized as usual. Commercially available phenolic compounds may also be used.

For the adhesive according to the present invention, the amount of the component (C) is preferably from 3 to 20 parts by mass, more preferably from 5 to 15 parts by mass, even more preferably from 5 to 10 parts by mass per 100 parts by mass of the epoxy resin. By setting the amount within these ranges, it is possible to achieve a sufficiently strong curing acceleration effect without worsening the physical properties of the cured product.

For the adhesive according to the present invention, the ratio between the amounts of the components (B) and (C) is preferably from 30:1 to 1.5:1 (component (B):component (C)), more preferably from 10:1 to 2:1 (component (B): component (C)), even more preferably from 8:1 to 4:1 (component (B):component (C)), in parts by mass.

(D) Mineral Filler

The adhesive according to the present invention may contain a mineral filler as the component (D).

Examples of mineral fillers include so-called inorganic fillers, such as alumina (aluminum oxide), magnesia (magnesium oxide), titanium oxide (titanium white), aluminum hydroxide, barium titanate, zinc oxide, silica (including crystalline silica (silicon oxide) and fused silica (silicon oxide)), metal nanoparticles, and glass fiber; layered silicates, such as talc, clay, mica, smectite, kaolin minerals, mica clay, and vermiculite; metal powders, such as silver and copper powders; and nitrides, such as aluminum nitride, boron nitride, silicon nitride, and gallium nitride. Materials such as silicon carbide, carbon black, graphite, carbon fiber, and carbon nanotubes can also be used.

It is also preferred that these mineral fillers have undergone surface treatment. Such a surface treatment is not particularly limited. An example is surface treatment with a silane compound. In the present invention, "silane compound" refers to a compound having a structure in which at least one organic group is attached to Si. $SiR_4$ (where $R_4$ represents organic groups) is more preferred. For use as the silane compound, silane coupling agents, silazanes, and silicone compounds (polysiloxanes) are preferred. Such a surface treatment method can be performed as usual. For example, paragraphs to of JP2018-195964A can be referred to.

The mineral fillers listed above are commercially available. For instance, examples of commercially available alumina include DAM-70, DAM-45, DAM-07, DAM-05, DAW-45, DAW-05, DAW-03, and ASFP-20 (all are trade names; manufactured by Denki Kagaku Kogyo), AL-43-KT, AL-47-H, AL-47-1, AL-160SG-3, AL-43-BE, AS-30, AS-40, AS-50, AS-400, CB-P02, and CB-P05 (all are trade names; manufactured by Showa Denko), A31, A31B, A32, A33F, A41A, A43A, MM-22, MM-26, MM-P, MM-23B, LS-110F, LS-130, LS-210, LS-242C, LS-250, and AHP300 (all are trade names; manufactured by Nippon Light Metal), AA-03, AA-04, AA-05, AA-07, AA-2, AA-5, AA-10, and AA-18 (all are trade names; manufactured by Sumitomo Chemical), and AEROXIDE Alu C, AEROXIDE Alu C805, and AEROXIDE Alu 65 (all are trade names; manufactured by Nippon Aerosil).

Examples of commercially available titanium oxides include G-1, G-10, F-2, F-4, and F-6 (all are trade names; manufactured by Showa Denko), TAF-520, TAF-500, TAF-1500, TM-1, TA-100C, and TA-100CT (all are trade names; manufactured by Fuji Titanium Industry), MT-01, MT-10EX, MT-05, MT-100S, MT-100TV, MT-100Z, MT-150EX, MT-100AQ, MT-100WP, MT-100SA, MT-100HD, MT-300HD, MT-500SA, MT-600SA, and MT-700HD (all are trade names; manufactured by Tayca), TTO-51 (A), TTO-51 (C), TTO-55 (A), TTO-55 (B), TTO-55 (C), TTO-55 (D), TTO-S-1, TTO-S-2, TTO-S-3, TTO-S-4, MPT-136, and TTO-V-3 (all are trade names; manufactured by Ishihara Sangyo Kaisha), and AEROXIDE NKT90 (trade names, manufactured by Nippon Aerosil).

Examples of commercially available aluminum hydroxides include B-309 and B-309 (both are trade names; manufactured by Tomoe Engineering) and BA173, BA103, B703, B1403, BF013, BE033, BX103, and BX043 (all are trade names; manufactured by Nippon Light Metal).

Examples of commercially available layered silicates include NANO ACE D-1000, NANO ACE D-800, MICRO ACE SG-95, MICRO ACE P-8, and MICRO ACE P-6 (all are trade names of talc products; manufactured by Nippon Talc), FH104, FH105, FL108, FG106, MG115, FH104S, and ML112S (all are trade names of talc products; manufactured by Fuji Talc), Y-1800, TM-10, A-11, and SJ-005 (all are trade names of mica products; manufactured by Yamaguchi Mica), and KUNIVIS-110 (trade name, manufactured by Kunimine Industries).

Examples of commercially available barium titanates include BT-H9DX, HF-9, HF-37N, HF-90D, HF-120D, and HT-F (all are trade names; manufactured by KCM), BT-100 and HPBT series (both are trade names; manufactured by Fuji Titanium Industry), BT series (manufactured by Sakai Chemical Industry), and PAL SERUM BT (manufactured by Nippon Chemical Industrial).

Examples of commercially available zinc oxides include FINEX-30, FINEX-30W-LP2, FINEX-50, FINEX-50S-LP2, and XZ-100F (all are trade names; manufactured by Sakai Chemical Industry), FZO-50 (manufactured by Ishihara Sangyo Kaisha), and MZ-300, MZ-306X, MZY-505S, MZ-506X, and MZ-510HPSX (all are trade names; manufactured by Tayca).

Examples of commercially available glass fibers include CS6SK-406, CS13C-897, CS3PC-455, and CS3LCP-256 (all are trade names; manufactured by Nitto Boseki), ECS03-615, ECS03-650, EFDE50-01, and EFDE50-31 (all are trade names; manufactured by Central Glass), and ACS6H-103 and ACS6S-750 (both are trade names; manufactured by Nippon Electric Glass).

Examples of commercially available metal powders include AG3 and AG4, which are spherical silver powders, and FA5 and FA2, which are flaky silver powders (all are trade names; manufactured by DOWA Hightech), SPQ03R, SPN05N, SPN08S, and Q03R (all are trade names of silver powder products; manufactured by Mitsui Mining & Smelting), AY-6010 and AY-6080 (both are trade names of silver powder products; manufactured by Tanaka Kikinzoku Kogyo), ASP-100 (trade name of a silver powder product, manufactured by Aida Chemical Industries), AG/SP Ag-coated powder (trade name of a silver powder product, manufactured by Mitsubishi Materials Electronic Chemicals), MA-O015K, MA-O02K, MA-O025K (all are trade names of copper powder products; manufactured by Mitsui Mining & Smelting), #52-C and #6 electrolytic copper powders (manufactured by JX Nippon Mining & Metals), 10% Ag-coated Cu-HWQ (trade name of a copper powder product, manufactured by Fukuda Metal Foil & Powder), Type-A and Type-B (both are trade names of copper powder products; manufactured by DOWA Electronics Materials), and UCP-030 (trade name of a copper powder product, manufactured by Sumitomo Metal Mining).

Examples of commercially available nitrides include H-Grade, E-Grade, and H-T-Grade (all are trade names of aluminum nitride products; manufactured by Tokuyama), TOYAL TecFiller TFS-A05P and TOYAL TecFiller TFZ-A02P (both are trade names of aluminum nitride products; manufactured by Toyo Aluminium), ALN020BF, ALN050BF, ALN020AF, ALN050AF, and ALN020SF (all are trade names of aluminum nitride products; manufactured by Tomoe Engineering), FAN-f05 and FAN-f30 (both are trade names of aluminum nitride products; manufactured by Furukawa Denshi), Denka Boron Nitride SGP, Denka Boron Nitride MGP, Denka Boron Nitride GP, Denka Boron Nitride HGP, Denka Boron Nitride SP-2, and Denka Boron Nitride SGPS (all are trade names of boron nitride products; manufactured by Denki Kagaku Kogyo), UHP-S1, UHP-1K, UHP-2, and UHP-EX (all are trade names of boron nitride products; manufactured by Showa Denko), and SN-9, SN-9S, SN-9FWS, SN-F1, and SN-F2 (all are trade names of silicon nitride products; manufactured by Denki Kagaku Kogyo).

Examples of commercially available glass fibers include CF0027, CF0093, CF0018, and CF0033 (all are trade names; manufactured by Nippon Frit).

Examples of commercially available silicon carbides include GMF-H Type, GMF-H2 Type, and GMF-LC Type (all are trade names; manufactured by Pacific Rundum) and HSC1200, HSC1000, HSC059, HSC059I, and HSC007 (all are trade names; manufactured by Tomoe Engineering).

Examples of commercially available silica include SYLYSIA (manufactured by Fuji Sylisia Chemical), AEROSIL R972, AEROSIL R104, AEROSIL R202, AEROSIL 805, AEROSIL R812, AEROSIL RX200, AEROSIL R9200, AEROSIL NAX50, AEROSIL 200, and AEROSIL R7200 (all are trade names; manufactured by Nippon Aerosil), REOLOSIL series (manufactured by Tokuyama), CMC-12, VX-S, and VX-SR (all are trade names of crystalline silica products; manufactured by Tatsumori), FB-3SDC, FB-3SDX, SFP-30M, SFP-20M, SFP-30MHE, SFP-130MC, and UFP-30 (all are trade names of fused silica products; manufactured by Denki Kagaku Kogyo), and EXCELICA series (trade name of fused silica products, manufactured by Tokuyama).

Examples of commercially available carbon fibers, carbon black, graphite, and carbon nanotubes include TORAYCA MLD-30 milled fiber and TORAYCA MLD-300 milled fiber (both are trade names of carbon fiber products; manufactured by Toray Industries), CFMP-30X and CFMP-150X (both are trade names of carbon fiber products; manufactured by Nihon Polymer), #1000 (trade name of a carbon black product; manufactured by Mitsubishi Chemical), XN-100 and HC-600 (both are trade names of graphite products; manufactured by Nippon Graphite Fiber), and SWeNT SG65, SWeNT SGi, IsoNanoTubes-M, IsoNanoTubes-S, PureTubes, Pyrograf PR-25-XT-PS, and PR-25XT-LHT (all are trade names of carbon nanotube products; manufactured by Sigma-Aldrich).

The mineral filler used in the adhesive according to the present invention is preferably at least one of silica (preferably fumed silica), titanium oxide, alumina, or a layered silicate, more preferably silica. Preferably, these fillers have been hydrophobized through surface treatment for improved chemical resistance. Mineral fillers with at least alkyl groups introduced to their surface through surface treatment, or alkyl-modified mineral fillers, are more preferred. In particular, surface-treated silica (preferably alkyl-modified silica particles) is suitable.

The mineral filler used in the present invention preferably has a volume-average particle diameter (average diameter of primary particles) of 1 to 10000 nm, more preferably 3 to 5000 nm, even more preferably 5 to 2000 nm, still more preferably 5 to 1000 nm, still even more preferably 6 to 500 nm, further preferably 7 to 200 nm, particularly preferably 8 to 100 nm. For silica, titanium oxide, and alumina, the volume-average particle diameter is preferably from 1 to 500 nm, more preferably from 5 to 200 nm, even more preferably from 6 to 100 nm, particularly preferably from 7 to 50 nm for chemical resistance of the cured product.

The mineral filler is added to methanol so that the filler concentration will be 0.5% by mass. The mineral filler is dispersed by 10 minutes of sonication. The particle size distribution of the mineral filler treated in such a manner is measured using a laser scattering particle size distribution analyzer (manufactured by HORIBA; trade name, LA950V2), and the volume-based median diameter is determined. The median diameter corresponds to the particle diameter in a cumulative particle size distribution at which the cumulative percentage is 50%.

For the adhesive according to the present invention, the amount of the component (D) is preferably from 4% to 20% by mass, more preferably from 4% to 15% by mass, even more preferably from 4% to 12% by mass for the viscosity of the adhesive.

For the adhesive according to the present invention, the amount of the component (D) can be from 1 to 50 parts by mass, preferably is from 4 to 20 parts by mass, per 100 parts by mass of the epoxy resin as the component (A).

The mineral filler as the component (D) is preferably dispersed homogeneously in the adhesive after the components (A) to (C) are mixed together (before curing).

The adhesive according to the present invention preferably has a viscosity of 30 Pa·s or more and less than 2500 Pa·s, more preferably 200 or more and less than 1500 Pa·s, even more preferably 350 to 1350 Pa·s, particularly preferably 500 to 1100 Pa·s because it is to be used in the manufacture of a medical device. The viscosity is a value determined by the measuring method described in the Examples section below.

For the same reason, the adhesive according to the present invention preferably exhibits a percentage degree of cure, as defined in the Examples section below, of 70% or more, preferably 80% or more, more preferably 90% or more.

Cured Product

A cured product according to the present invention is a cured product that forms through the curing of the adhesive according to the present invention. The cured product according to the present invention, therefore, is used as a member that forms a bonded section of a medical device or a constituent member of a medical device. The curing temperature of the adhesive according to the present invention is not particularly limited and can be set as appropriate according to the component (B) contained in the adhesive according to the present invention. The mixing of the components can be carried out as usual. This mixing process is preferably carried out while bubbles are removed and is, therefore, typically performed under reduced pressure.

Specifically, the adhesive according to the present invention can efficiently undergo a curing reaction and give a cured product according to the present invention even at low temperatures. The curing temperature is preferably, for example, 100° C. or lower, more preferably 80° C. or lower, even more preferably 60° C. or lower, particularly preferably 50° C. or lower. The adhesive can even be cured at or below room temperature (25° C.), which is also preferred. The curing temperature is preferably 15° C. or higher, more preferably 20° C. or higher, so that the curing reaction will proceed sufficiently. The duration of the curing reaction can be set as appropriate according to the purpose(s). Typically, the adhesive undergoes a curing reaction for 1.5 to 200 hours to give the cured product.

By setting the curing temperature within the above ranges, it is possible to achieve a sufficiently strong curing acceleration effect and inhibit the reaction between the components (C) and (A) at the same time.

For a reduced chance of repeated exposure to high temperatures of the medical device during its manufacturing process, too, this curing temperature of the adhesive according to the present invention is preferably set as low as possible.

Medical Device Member

In the following, a medical device member 10 (hereinafter, a "medical device member" is also simply referred to as a "member") according to the present invention has a substrate 1 and a cured product 2 (cured product according to the present invention) on the substrate.

The reference numerals in the foregoing correspond to the reference numerals in FIG. 1.

Substrate

The substrate that the medical device member according to the present invention has is not particularly limited and can be selected from a wide range of substrates that are used as constituent members of ordinary medical devices.

Specifically, the substrate preferably includes, for example, a metal (iron or a nonferrous metal), an inorganic material other than metals, or an organic material, more preferably includes a metal (is a metal substrate).

The iron includes an alloy of iron and a nonferrous metal. An example of such an alloy is stainless steel, and stainless steel is preferred for use in the present invention.

Examples of nonferrous metals include aluminum, titanium, magnesium, nickel, copper, lead, zinc, tin, chromium, tungsten, cobalt, vanadium, and gold and alloys of at least two of these. Aluminum, titanium, magnesium, nickel, copper, lead, zinc, tin, chromium, tungsten, and cobalt and alloys of at least two of these are preferred.

Examples of inorganic materials other than metals include glass and glass ceramics.

Examples of types of glass include soda-lime glass, Pyrex® glass, quartz glass, and non-alkaline glass.

Examples of glass ceramics include alumina, zirconia, silicon carbide, and silicon nitride.

Examples of organic materials include thermoplastic resins and thermosetting resins.

Examples of thermoplastic resins include thermoplastic polyimide resins, thermoplastic polyamide resins, polyetherimide resins, polyphenylene ether resins, polycarbonate resins, polyethylene terephthalate resins, polyethylene naphthalate resins, polyphenylene sulfide resins, polyether ether ketone resins, polyethersulfone resins, acrylic resins, and polyolefin resins, such as polyethylene resins, polypropylene resins, and polymethylpentene resins, and thermoplastic polycycloolefins, such as thermoplastic polynorbornene.

Examples of thermosetting resins include thermosetting polyimide resins, thermosetting polyamide resins, polyamide-imide resins, epoxy resins, phenolic resins, styrene resins, such as polystyrene resins, ABS resins (acrylonitrile-butadiene-styrene copolymer resins), and acrylonitrile-styrene copolymer resins, and thermosetting polycycloolefins, such as thermosetting polynorbornene.

The physical properties, such as flexibility and stiffness, of the substrate can be determined as appropriate according to the medical device to which the member is applied. The same applies to the thickness of the substrate. The thickness of the substrate can be, for example, from 0.1 to 50 mm and may be from 0.5 to 10 mm.

The shape of the substrate, furthermore, is not particularly limited. The substrate may have irregularities and may have recesses. The adhesive according to the present invention is superior in shape retention and can thus retain its shape during curing even after being thickly applied. With the adhesive, therefore, precise sealing is possible independently of, for example, the shape of recesses of the substrate. It is also possible to produce a desired structure (e.g., a desired shape of protrusions) by curing the adhesive. The adhesive according to the present invention, therefore, is also suitable for use as a resin material or resin composition for obtaining a resin structure (article shaped from resin).

The amount of at least one of a metal, an inorganic material other than metals, or an organic material included in the substrate is not particularly limited. It can be, for example, 80% by mass or more, preferably is 90% by mass or more, and may even be 100% by mass.

Medical Device

Examples of medical devices including a constituent member secured with a cured product according to the present invention and medical devices to which a member according to the present invention is applicable, or medical devices according to the present invention, include catheters, applicators, X-ray imaging devices, electric operation devices, active instruments for treatment, ultrasound diagnostic apparatuses, and endoscopes.

Endoscope

In one embodiment, an endoscope according to the present invention has a medical device member according to the present invention as its constituent member.

In another embodiment, an endoscope according to the present invention includes a constituent member secured with a cured product according to the present invention. "A constituent member secured with a cured product according to the present invention" means that at least a subset of the members forming the endoscope has been secured to a support member with the cured product according to the present invention therebetween.

Method for Manufacturing a Medical Device

A medical device according to the present invention can be manufactured as usual, for example, except that an adhesive according to the present invention is used. For example, it can be manufactured with reference to WO2020/175272A, JP2009-194934A, JP2014-511191A, and JP2001-128929A.

EXAMPLES

The present invention will now be more specifically described based on the following examples. It should be noted that the present invention should not be interpreted to be limited to the examples except as specified in the present invention.

Preparation of Epoxy Resin Adhesives

Preparation of Epoxy Resin Adhesive 1 (Epoxy Resin Adhesive No. 1 in Table 1 Below)

Epoxy resin adhesive 1 was obtained by mixing 10.0 parts by mass of bisphenol A diglycidyl ether (trade name, jER 828; manufactured by Mitsubishi Chemical; epoxy equivalent, 189) (component A-1 in Table 1 below), 1.5 parts by mass of hexamethylenediamine (component B-1 in Table 1 below), 0.6 parts by mass of MEH-8000H (trade name, manufactured by Meiwa Plastic Industries) (component C-5 in Table 1 below), and 1.5 parts by mass of AEROSIL NAX50 (trade name; manufactured by Nippon Aerosil; average diameter of primary particles, 30 nm) (component D-2 in Table 1 below), and defoaming the mixture for 5 minutes with "THINKY MIXER ARV-310 (trade name, manufactured by Thinky)" while stirring them at 2000 rpm at 25° C. under a reduced pressure of 1.0 Pa.

Preparation of Epoxy Resin Adhesives 2 to 28 and c1 to c7 (Epoxy Resin Adhesives Nos. 2 to 28 and c1 to c7 in Table 1 Below)

Epoxy resin adhesives 2 to 28 and c1 to c7 were prepared in the same manner as epoxy resin adhesive 1, except that the formula of epoxy resin adhesive 1 in the preparation of epoxy resin adhesive 1 was changed to the formulae of epoxy resin adhesives 2 to 28 and c1 to c7, presented in Table 1 below.

Testing

As-prepared epoxy resin adhesives 1 to 28 and c1 to c7 were subjected to the following tests (test examples 1 to 4). The results are summarized in Table 1 (Tables 1-1 to 1-4) below.

Test Example 1: Working Life

Each epoxy resin adhesive was allowed to stand at 25° C. After 25 minutes and 45 minutes from the start of standing, the epoxy resin adhesive was pushed with a needle, and its working life was evaluated on the following evaluation scale.

Evaluation Scale

- S: There is no stringiness after both 25 minutes and 45 minutes.
- A: There is no stringiness after 25 minutes, and minor stringiness is observed after 45 minutes. Usable without a problem as an adhesive even after 45 minutes from preparation.
- B: Stringiness is observed after 25 minutes. Usable without a problem as an adhesive even after 25 minutes from preparation.
- C: Stringiness is severe (curing has proceeded) after 25 minutes. Not usable as an adhesive after 25 minutes from preparation.

Test Example 2: Curability

Curability

The amount of heat (I) generated by 5 mg of each as-prepared epoxy resin adhesive and the amount of heat (II) generated by the epoxy resin adhesive heated at 60° C. for 2 hours immediately after preparation were measured using DSC-1 (trade name, manufactured by Mettler Toledo, differential scanning calorimetry). The percentage degree of cure (%) was calculated by incorporating the measured amounts of heat into the following formula.

$$\text{Percentage degree of cure}=100\times\{\text{amount of heat }(I)-\text{amount of heat }(II)\}/\text{amount of heat }(I)$$

The calculated percentage degree of cure was evaluated by comparing it to the following evaluation scale. An adhesive with a higher percentage degree of cure is better because an insufficient percentage degree of cure causes stickiness, for example, when the adhesive is used to assemble a medical device.

Evaluation Scale

- S: The percentage degree of cure is 90% or more
- A: The percentage degree of cure is 80% or more and less than 90%

B: The percentage degree of cure is 70% or more and less than 80%

C: The percentage degree of cure is less than 70%

Test Example 3: Viscosity

The viscosity of each epoxy resin adhesive was measured using a Mars 40 (trade name) rheometer manufactured by Thermo Fisher Scientific. The geometry was 20-mm diameter aluminum parallel plates. The temperature condition was 25° C. Measurement was carried out at a shear rate of 0.01/sec under rotational deformation.

Test Example 4: Shape Retention

Each epoxy resin adhesive was shaped into a 5-mm diameter dome on a 10-mm wide×40-mm long×1-mm thick stainless steel (SUS) sheet and allowed to stand for 10 minutes at 25° C. The shape after 10 minutes was visually observed and evaluated by comparing it to the following evaluation scale.

Evaluation Scale

S: The shape remains unchanged.

A: The shape has changed very slightly.

B: The shape has changed slightly, but the initial shape can be restored by pushing with a needle.

C: The dome totally failed to maintain its shape.

Preparation of Test Specimens

Figure 2:
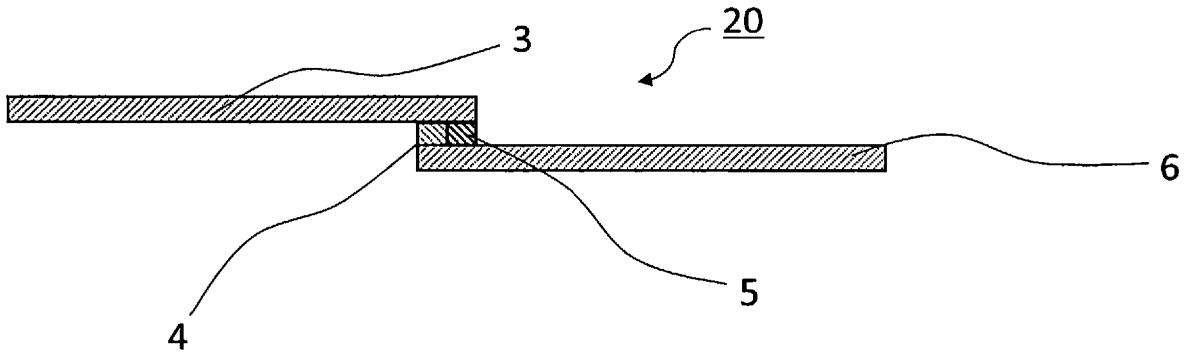
FIG. 2 is a cross-sectional view schematically illustrating a test specimen prepared in the Examples.

For each example or comparative example, three test specimens as illustrated in FIG. 2 were prepared as described below for test examples 5 and 6-1 below.

The as-prepared epoxy resin adhesives were each applied to a SUS sheet 3 (40 mm long×5 mm wide×1 mm thick) to achieve a size of 0.08 mm in thickness, 5 mm in length, and 5 mm in width. Another SUS sheet 6 was joined, and the adhesive was cured at 80° C. for 12 hours to give a test specimen 20 formed by the SUS sheets 3 and 6 and a cured product 4 of the epoxy resin adhesive sandwiched therebetween (the size of the overlap between the two SUS sheets was 5 mm in length and 5 mm in width).

The spacer 5 was a 0.08-mm thick Teflon® sheet.

Testing

Each test specimen was subjected to the following tests (test examples 5 and 6-1). The results are summarized in Table 1 below.

Test Example 5: Chemical Resistance

Each test specimen was immersed in ESCIDE disinfectant (trade name, manufactured by FUJIFILM Medical, an aqueous solution containing 6% by mass peracetic acid) for 24 hours at 40° C. After immersion, the test specimen was washed with water, drops of water were wiped off, and then the appearance of the cured product of the epoxy resin adhesive was observed.

Evaluation Scale

S: No change is seen even in observation with a magnifying glass having a magnification of 3×.

A: Slight cracking is seen in observation with a magnifying glass having a magnification of 3×, but no cracking is seen in visual observation.

B: Slight cracking is seen in visual observation.

C: A crack that extends to the inside of the film is seen in visual observation.

Test Example 6-1: Sterilization Durability

The test specimens were subjected to a hydrogen peroxide plasma sterilization treatment by operating STERRAD® NX (trade name, manufactured by Johnson & Johnson) to perform 100 "ADVANCED" sterilization cycles.

Before and after the sterilization treatment, the shear bonding strength of each test specimen was measured. Specifically, each test specimen was subjected to stretching from both sides at a test speed of 2 mm/min with a fixture-to-fixture distance of 50 mm, and its bonding strength was measured. This test was performed using an AGS-X tabletop precision universal tester (trade name, manufactured by Shimadzu) in a 23° C. environment.

The percentage maintenance of shear bonding strength (%) was calculated by incorporating the shear bonding strength (I) (MPa) of the test specimen before the sterilization treatment and the shear bonding strength (II) (MPa) of the test specimen after the sterilization treatment into the following formula.

$$\text{Percentage maintenance of shear bonding strength } (\%) = 100 \times (II)/(I)$$

Sterilization durability was evaluated by comparing the calculated percentage maintenance of shear bonding strength (%) to the following evaluation scale.

Evaluation Scale

S: 90% or more

A: 80% or more and less than 90%

B: 70% or more and less than 80%

C: 60% or more and less than 70%

D: Less than 60%

Test Example 6-2: Sterilization Durability

Using epoxy resin adhesive 8 and the substrates listed in Table 2 below, test specimens each having one of the substrates listed in Table 2 below were prepared as in "Preparation of Test Specimens" above. Two test specimens were prepared per substrate. Each test specimen was subjected to the same test as in test example 6-1. The results are presented in Table 2 below.

TABLE 1-1

| | | No. 1 | No. 2 | No. 3 | No. 4 | No. 5 | No. 6 | No. 7 | No. 8 | No. 9 | No. 10 | No. 11 | No. 12 | No. 13 | No. 14 | No. 15 | No. 16 | No. 17 | No. 18 |
|---|---|---|---|---|---|---|---|---|---|---|---|---|---|---|---|---|---|---|---|
| (A) | A-1 | 10.0 | 10.0 | | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 |
| | A-2 | | | 10.0 | | | | | | | | | | | | | | | |
| (B) | B-1 | 1.5 | | 1.7 | | | | | | | | | | | | | | | |
| | B-2 | | 2.6 | | | | | | | | | | | | | | | | |
| | B-3 | | | | 2.1 | 2.1 | 2.1 | 2.1 | 2.1 | 2.1 | 2.1 | 2.1 | 2.1 | 2.1 | 2.1 | 2.1 | 2.1 | 2.1 | 2.1 |
| | B-4 | | | | | | | | | | | | | | | | | | |
| | B-5 | | | | | | | | | | | | | | | | | | |
| | B-6 | | | | | | | | | | | | | | | | | | |
| | B-7 | | | | | | | | | | | | | | | | | | |
| | B-8 | | | | | | | | | | | | | | | | | | |
| | B-9 | | | | | | | | | | | | | | | | | | |
| | B-10 | | | | | | | | | | | | | | | | | | |
| | B-11 | | | | | | | | | | | | | | | | | | |
| | B-12 | | | | | | | | | | | | | | | | | | |
| (C) | C-1 | | | | 0.6 | | | | | | | | | | | | | | |
| | C-2 | | | | | 0.6 | | | | | | | | | | | | | |
| | C-3 | | | | | | 0.6 | | | | | | | | | | | | |
| | C-4 | | | | | | | 0.6 | | | | | | | | | | | |
| | C-5 | 0.6 | 0.6 | 0.6 | | | | | 0.6 | | 0.6 | 0.6 | 0.6 | 0.6 | 0.6 | 0.3 | 1.2 | 1.5 | |
| | C-6 | | | | | | | | | 0.6 | | | | | | | | | 0.6 |
| (P) | P-1 | | | | | | | | | | | | | | | | | | |
| | P-2 | | | | | | | | | | | | | | | | | | |
| | P-3 | | | | | | | | | | | | | | | | | | |
| | P-4 | | | | | | | | | | | | | | | | | | |
| | P-5 | | | | | | | | | | | | | | | | | | |
| | P-6 | | | | | | | | | | | | | | | | | | |
| (Q) | Q-1 | | | | | | | | | | | | | | | | | | |
| (D) | D-1 | | | | | | | | | | 0.6<br>(4.5) | 0.3<br>(2.3) | | | | | | | 0.6<br>(4.5) |
| | D-2 | 1.5<br>(11.0) | 1.5<br>(10.2) | 1.5<br>(10.9) | 1.5<br>(10.6) | (10.6)<br>1.5 | 1.5<br>(10.6) | 1.5<br>(10.6) | 1.5<br>(10.6) | 1.5<br>(10.6) | | | 4.0<br>(23.9) | | | 1.5<br>(10.8) | 1.5<br>(10.1) | 1.5<br>(9.9) | |
| | D-3 | | | | | | | | | | | | | 1.0<br>(7.3) | | | | | |
| | D-4 | | | | | | | | | | | | | | 0.6<br>(4.5) | | | | |

TABLE 1-2

| | No. 1 | No. 2 | No. 3 | No. 4 | No. 5 | No. 6 | No. 7 | No. 8 | No. 9 | No. 10 | No. 11 | No. 12 | No. 13 | No. 14 | No. 15 | No. 16 | No. 17 | No. 18 |
|---|---|---|---|---|---|---|---|---|---|---|---|---|---|---|---|---|---|---|
| Working life | S | S | S | S | S | S | S | S | S | S | S | S | S | S | S | A | B | S |
| Curability | S | S | S | S | S | S | S | S | S | S | S | S | S | S | S | S | S | S |
| Viscosity (Pa · s) | 900 | 900 | 900 | 900 | 900 | 900 | 900 | 900 | 850 | 1000 | 300 | 2200 | 150 | 1000 | 900 | 900 | 900 | 900 |
| Shape retention | A | A | A | A | A | A | A | A | B | A | B | B | A | B | A | A | A | B |
| Chemical resistance | A | A | B | A | A | A | A | S | B | S | S | A | B | B | A | S | S | B |
| Sterilization durability (SUS sheets) | A | A | A | A | A | A | B | S | B | S | S | S | S | S | A | S | S | B |

TABLE 1-3

| | | No. 19 | No. 20 | No. 21 | No. 22 | No. 23 | No. 24 | No. 25 | No. 26 | No. 27 | No. 28 | No. c1 | No. c2 | No. c3 | No. c4 | No. c5 | No. c6 | No. c7 |
|---|---|---|---|---|---|---|---|---|---|---|---|---|---|---|---|---|---|---|
| (A) | A-1 | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 | 10.0 |
| | A-2 | | | | | | | | | | | | | | | | | |
| (B) | B-1 | | | | | | | | | | | | | | | | | |
| | B-2 | | | | | | | | | | | | | | | | | |
| | B-3 | | | | | | | | | | 2.1 | | | | | | | 2.1 |
| | B-4 | 1.5 | | | | | | | | | | | | | | | | |
| | B-5 | | 1.9 | | | | | | | | | | | | | | | |
| | B-6 | | | 5.3 | | | | | | | | | | | | | | |
| | B-7 | | | | 1.8 | | | | | | | | | | | | | |
| | B-8 | | | | | 2.3 | | | | | | | | | | | | |
| | B-9 | | | | | | 2.2 | | | | | | | | | | | |
| | B-10 | | | | | | | 2.8 | | | | | | | | | | |
| | B-11 | | | | | | | | 3.2 | | | | | | | | | |
| | B-12 | | | | | | | | | 1.4 | | | | | | | | |
| (C) | C-1 | | | | | | | | | | | | | | | | | |
| | C-2 | | | | | | | | | | | | | | | | | |
| | C-3 | | | | | | | | | | | | | | | | | |
| | C-4 | | | | | | | | | | | | | | | | | |
| | C-5 | 0.6 | 0.6 | 0.8 | 0.6 | 0.6 | 0.6 | 0.7 | 0.7 | 0.6 | 0.6 | 1.1 | 0.9 | 0.6 | 0.6 | 0.6 | 0.6 | |
| | C-6 | | | | | | | | | | | | | | | | | |
| (P) | P-1 | | | | | | | | | | | 12.0 | | | | | | |
| | P-2 | | | | | | | | | | | | 7.0 | | | | | |
| | P-3 | | | | | | | | | | | | | 0.6 | | | | |
| | P-4 | | | | | | | | | | | | | | 0.6 | | | |
| | P-5 | | | | | | | | | | | | | | | 7.0 | | |
| | P-6 | | | | | | | | | | | | | | | | 0.6 | |
| (Q) | Q-1 | | | | | | | | | | | | | | | | | 0.6 |
| (D) | D-1 | | | | | | | | | | | | | | | | | |
| | D-2 | 1.5 (11.0) | 1.5 (10.7) | 1.5 (8.5) | 1.5 (10.8) | 1.5 (10.4) | 1.5 (10.5) | 1.5 (10.0) | 1.5 (9.8) | 1.5 (11.1) | | 1.5 (6.1) | 1.5 (7.7) | 1.5 (11.8) | 1.5 (11.8) | 1.5 (7.9) | 1.5 (11.8) | 1.5 (10.6) |
| | D-3 | | | | | | | | | | | | | | | | | |
| | D-4 | | | | | | | | | | | | | | | | | |

TABLE 1-4

| | No. 19 | No. 20 | No. 21 | No. 22 | No. 23 | No. 24 | No. 25 | No. 26 | No. 27 | No. 28 | No. c1 | No. c2 | No. c3 | No. c4 | No. c5 | No. c6 | No. c7 |
|---|---|---|---|---|---|---|---|---|---|---|---|---|---|---|---|---|---|
| Working life | S | S | S | S | S | S | S | S | S | S | S | S | S | S | S | S | B |
| Curability | B | B | B | S | A | A | A | A | B | S | C | S | C | C | C | C | S |
| Viscosity (Pa · s) | 900 | 900 | 600 | 900 | 1900 | 1900 | 900 | 900 | 900 | 50 | 150 | 400 | 900 | 900 | 400 | 900 | 900 |
| Shape retention | A | A | A | A | A | A | A | A | A | B | B | B | A | A | A | A | A |
| Chemical resistance | B | B | B | B | B | B | B | B | B | S | C | C | C | C | C | C | C |
| Sterilization durability (SUS sheets) | B | B | B | B | B | B | B | B | B | S | D | D | D | D | D | D | D |

Notes for the Tables

The amounts in the tables are in parts by mass. For the component (D), the percentage in the adhesive (% by mass) is indicated under the amount.

It should be noted that the amount of a component represents the quantity of the component itself. If the raw material includes a solvent, therefore, the amount excludes the quantity of the solvent.

Component (A): Epoxy Resin

A-1:

Bisphenol A diglycidyl ether (trade name, jER 828; manufactured by Mitsubishi Chemical; epoxy equivalent, 189)

A-2:

An epoxy novolac resin (model number, 406775; Aldrich; epoxy equivalent, 165 to 175)

Component (B): Amine Compound having Two or More Unsubstituted Amino Groups

B-1:

Hexamethylenediamine

B-2:

1,12-Dodecanediamine

B-3:

Trimethylhexamethylenediamine

B-4:

1,3-Cyclohexanediamine

B-5:

1,3-Bis(aminomethyl)cyclohexane

B-6:

D-400 (trade name; manufactured by Tomoe Engineering; a compound represented by the chemical formula below; weight-average molecular weight, 430)

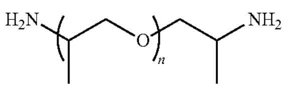

B-7:

m-Xylylenediamine

B-8:

p-Menthane-1,8-diamine

B-9:

Isophoronediamine

B-10:

4,4'-Methylenebis(cyclohexylamine)

B-11:

4,4'-Methylenebis(2-methylcyclohexylamine)

B-12:

m-Phenylenediamine

Component (C): Compound having a Nonaromatic Carbon-Carbon Double Bond Group and a Phenolic Hydroxy Group

C-1:

Sumilizer GM (trade name, manufactured by Sumitomo Chemical)

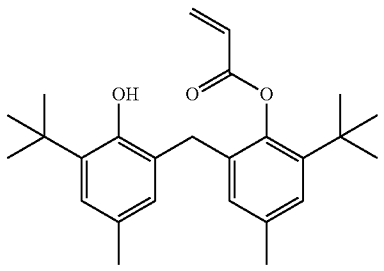 [SMILES: C=CC(=O)Oc1c(Cc2cc(C)cc(C(C)(C)C)c2O)cc(C)cc1C(C)(C)C]

C-2:

Sumilizer GS (trade name, manufactured by Sumitomo Chemical)

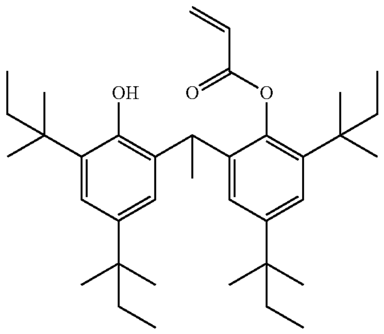 [SMILES: C=CC(=O)Oc1c(C(C)c2cc(C(C)(C)CC)cc(C(C)(C)CC)c2O)cc(C(C)(C)CC)cc1C(C)(C)CC]

C-3:

Triallylphenol

C-4:

o-Hydroxycinnamic acid

C-5:

MEH-8000H (trade name; manufactured by Meiwa Plastic Industries; average degree of polymerization, 2; weight-average molecular weight, 300)

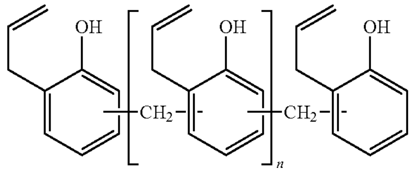

C-6:

p-Allylphenol

Component (P): Curing Agent Other Than Component (B)

P-1:

2-Octylsuccinic anhydride

P-2:

1,4-Butandiol bis(3-mercaptopropionate)

P-3:

1,2-Dimethylimidazole

P-4:

1,4-Bis(diphenylphosphino)butane

P-5:

Cresol novolac (trade name, PHENOLITE KA-1160; manufactured by DIC)

P-6:

N,N'-Dimethyl-1,6-diaminohexane

Component (Q): Compound having No Nonaromatic Carbon-Carbon Double Bond Group but having a Phenolic Hydroxy Group

Q-1:

Nonylphenol

Component (D): Filler

D-1:

AEROSIL RX200 (trade name; manufactured by Nippon Aerosil; average diameter of primary particles, 12 nm)

D-2:

AEROSIL NAX50 (trade name; manufactured by Nippon Aerosil; average diameter of primary particles, 30 nm)

D-3:

SFP-30M fused silica (trade name; manufactured by Denka; average diameter of primary particles, 700 nm)

D-4:

AEROSIL 200 (trade name; manufactured by Nippon Aerosil; average diameter of primary particles, 12 nm)

TABLE 2

| Substrate | Sterilization durability |
|---|---|
| Iron SPCC | A |
| Brass | A |
| Aluminum | A |
| Hot-dip galvanized steel sheet | B |
| Polystyrene | B |

Notes for the Table

Iron SPCC: manufactured by Standard Test Piece, a cold-rolled steel plate

Brass: manufactured by Standard Test Piece; model number, C2801

Aluminum: manufactured by Standard Test Piece; model number, A1050

Hot-dip galvanized steel sheet: manufactured by Standard Test Piece, a hot-dip galvanized steel sheet Polystyrene: manufactured by Standard Test Piece, a polystyrene sheet Adhesive Nos. c1 to c6 were made with an epoxy resin curing agent having no unsubstituted amino group. Cured products of these adhesives were inferior in chemical resistance and sterilization durability. Adhesive Nos. c1 and c3 to c6 were also inferior in curability.

Adhesive No. c7 was made with a compound having no nonaromatic carbon-carbon double bond group but having a phenolic hydroxy group. A cured product of this adhesive was inferior in chemical resistance and sterilization durability.

In contrast, as can be seen from the results, the adhesives according to the present invention (Nos. 1 to 28) had sufficiently high levels of characteristics that typical adhesives need to have (working life and shape retention before curing) and had rapid curability and viscosity suitable for the manufacture of a medical device. Cured products obtained through a curing reaction of these adhesives, furthermore, were superior in chemical resistance and sterilization durability.

While the present invention has been described in conjunction with embodiments thereof, we do not intend to limit our invention in any detail of the description unless otherwise specified. Rather, we believe that the invention should be broadly construed without departing from the spirit and scope of the invention as defined by the appended claims.

REFERENCE SIGNS LIST

1 substrate
2 cured product of epoxy resin adhesive
3 SUS sheet
4 cured product of epoxy resin adhesive
5 spacer
6 SUS sheet
10 medical device member
20 test specimen

What is claimed is:

1. An epoxy resin adhesive for a medical device, the epoxy resin adhesive comprising the following components (A) to (D):

(A) an epoxy resin;

(B) a polyamine compound having two or more unsubstituted amino groups;

(C) a compound having a nonaromatic carbon-carbon double bond group and a phenolic hydroxy group; and (D) mineral fillers having a volume-average particle diameter of 6 nm to 500 nm, wherein an amount of the component (D) in the epoxy resin adhesive is in a range of 4% to 20% by mass.

2. The epoxy resin adhesive for a medical device according to claim 1, wherein the nonaromatic carbon-carbon double bond group includes a vinyl group.

3. The epoxy resin adhesive for a medical device according to claim 1, wherein the component (C) includes a compound with an average degree of polymerization of 2 or greater.

4. The epoxy resin adhesive for a medical device according to claim 1, wherein the component (C) includes a compound having a substituent in an ortho position with respect to a ring-forming carbon atom, in an aromatic hydrocarbon ring, to which the phenolic hydroxy group is bonded.

5. The epoxy resin adhesive according to claim 1, wherein a ratio of an amount of the component (B) to an amount of the component (C) is in a range of 10:1 to 2:1.

6. A cured product obtained by curing the epoxy resin adhesive for a medical device according to claim 1.

7. A medical device member comprising a metal substrate and a cured product on the metal substrate, wherein the cured product is obtained by curing an epoxy resin adhesive comprising the following components (A) to (D):

(A) an epoxy resin;

(B) a polyamine compound having two or more unsubstituted amino groups;

(C) a compound having a nonaromatic carbon-carbon double bond group and a phenolic hydroxy group; and (D) mineral fillers having a volume-average particle diameter of 6 nm to 500 nm, wherein an amount of the component (D) in the epoxy resin adhesive is in a range of 4% to 20% by mass.

8. The medical device member according to claim 7, wherein the metal substrate is a stainless steel substrate.

9. A medical device comprising, as a constituent member, the medical device member according to claim 7.

10. A medical device comprising a constituent member secured with a cured product, wherein the cured product is obtained by curing an epoxy resin adhesive comprising the following components (A) to (D):

(A) an epoxy resin;

(B) a polyamine compound having two or more unsubstituted amino groups;

(C) a compound having a nonaromatic carbon-carbon double bond group and a phenolic hydroxy group; and (D) mineral fillers having a volume-average particle diameter of 6 nm to 500 nm, wherein an amount of the component (D) in the epoxy resin adhesive is in a range of 4% to 20% by mass.

11. The medical device according to claim 10, wherein the medical device is an endoscope.

12. The medical device according to claim 9, wherein the medical device is an endoscope.

* * * * *